(12) United States Patent
Kumar et al.

(10) Patent No.: US 11,867,654 B2
(45) Date of Patent: Jan. 9, 2024

(54) DEVICE AND METHOD FOR DETECTING CREATININE AND ALBUMIN TO CREATININE RATIO

(71) Applicant: INDIAN INSTITUTE OF SCIENCE, Bangalore (IN)

(72) Inventors: Vinay Kumar, Bangalore (IN); Navakanta Bhat, Bangalore (IN); Nikhila Kashyap Dhanvantari Madhuresh, Bangalore (IN)

(73) Assignee: Indian Institute of Science, Bangalore (IN)

( * ) Notice: Subject to any disclaimer, the term of this patent is extended or adjusted under 35 U.S.C. 154(b) by 660 days.

(21) Appl. No.: 15/573,686

(22) PCT Filed: Jan. 22, 2016

(86) PCT No.: PCT/IB2016/050311
§ 371 (c)(1),
(2) Date: Nov. 13, 2017

(87) PCT Pub. No.: WO2016/181229
PCT Pub. Date: Nov. 17, 2016

(65) Prior Publication Data
US 2018/0149612 A1 May 31, 2018

(30) Foreign Application Priority Data
May 12, 2015 (IN) .......................... 2412/CHE/2015

(51) Int. Cl.
*G01N 27/327* (2006.01)
*G01N 33/543* (2006.01)
(Continued)

(52) U.S. Cl.
CPC ....... *G01N 27/3277* (2013.01); *A61B 5/1468* (2013.01); *A61B 5/14507* (2013.01);
(Continued)

(58) Field of Classification Search
CPC ....... G01N 27/327–3277; G01N 27/48; G01N 33/493; G01N 33/5438; G01N 33/68;
(Continued)

(56) References Cited

U.S. PATENT DOCUMENTS 5,653,864 A * 8/1997 Gotoh ................ G01N 27/3273
205/792
2005/0287035 A1* 12/2005 Yon-Hin ................ C12Q 1/006
422/400

(Continued)

OTHER PUBLICATIONS

C. H. Chen, et al., A novel structural specific creatinine sensing scheme for the determination of the urine creatinine, Biosensors and Bioelectronics, vol. 31, pp. 90-94 (2012) (Year: 2012).*
(Continued)

*Primary Examiner* — J. Christopher Ball
(74) *Attorney, Agent, or Firm* — Meunier Carlin & Curfman LLC

(57) ABSTRACT

An electrochemically active, creatinine-binding device is provided to detect and measure quantitatively, creatinine in biological samples. The device of the present invention is also provided with a device to detect and measure quantitatively creatinine and albumin bioanalytes, simultaneously and to determine albumin to creatinine ratio (ACR). The present invention also provides an electrochemically active, creatinine-binding and albumin-binding device, for collection and retention of biological samples, having creatinine and albumin bioanalytes. In the present invention, a device holder is provided to receive the electrochemically active, creatinine-binding and albumin-binding device. The device, point-of-care biosensor and the method of the present invention, facilitate quantitative measurement of creatinine and (Continued)

albumin bioanalytes in urine and blood samples, and albumin to creatinine ratio (ACR), in urine samples, electrochemically, by determining redox current values.

20 Claims, 23 Drawing Sheets

(51) Int. Cl.
  G01N 33/493   (2006.01)
  A61B 5/145    (2006.01)
  A61B 5/1468   (2006.01)
  G01N 27/48    (2006.01)
  G01N 33/68    (2006.01)
  G01N 33/70    (2006.01)
(52) U.S. Cl.
  CPC ....... *A61B 5/14546* (2013.01); *G01N 27/327* (2013.01); *G01N 27/48* (2013.01); *G01N 33/493* (2013.01); *G01N 33/5438* (2013.01); *G01N 33/68* (2013.01); *G01N 33/70* (2013.01); *G01N 2333/76* (2013.01); *G01N 2333/765* (2013.01)
(58) Field of Classification Search
  CPC .............. G01N 33/70; G01N 2333/76; G01N 2333/765; A61B 5/14507; A61B 5/14546; A61B 5/1468; A61B 5/207; A61B 10/007; C07K 14/76
  See application file for complete search history.

(56) References Cited

U.S. PATENT DOCUMENTS

| | | |
|---|---|---|
| 2006/0191788 A1* | 8/2006 | Wayment ........... G01N 33/5438 204/403.01 |
| 2008/0076670 A1 | 3/2008 | Sivan et al. |
| 2010/0159606 A1* | 6/2010 | Nakaminami ......... G01N 33/70 436/73 |
| 2010/0291611 A1* | 11/2010 | Bolbot ............... G01N 33/6803 435/29 |
| 2012/0181189 A1 | 7/2012 | Merchant |
| 2012/0196379 A1* | 8/2012 | Azad .................... G01N 27/126 422/98 |
| 2014/0069823 A1 | 3/2014 | Winarta et al. |
| 2014/0170766 A1 | 6/2014 | Smith |
| 2014/0262776 A1 | 9/2014 | Martin et al. |

OTHER PUBLICATIONS

T. Yasukawa et al., A Dual Electrochemical Sensor Based on a Test-strip Assay for the Quantitative Determination of Albumin and Creatinine, Analytical Sciences, vol. 31, pp. 583-589 (2015) (Year: 2015).*

M. Mitewa, Coordination properties of the bioligands creatinine and creatine in various reaction media, Coordination Chemistry Reviews, vol. 140, pp. 1-25 (1995).*

International Search Report dated May 12, 2016, from International Application No. PCT/IB2016/50311, 1 page.

Notice of Intention to Grant relating to European Application No. 16 792 263.2, dated Sep. 16, 2020.

* cited by examiner

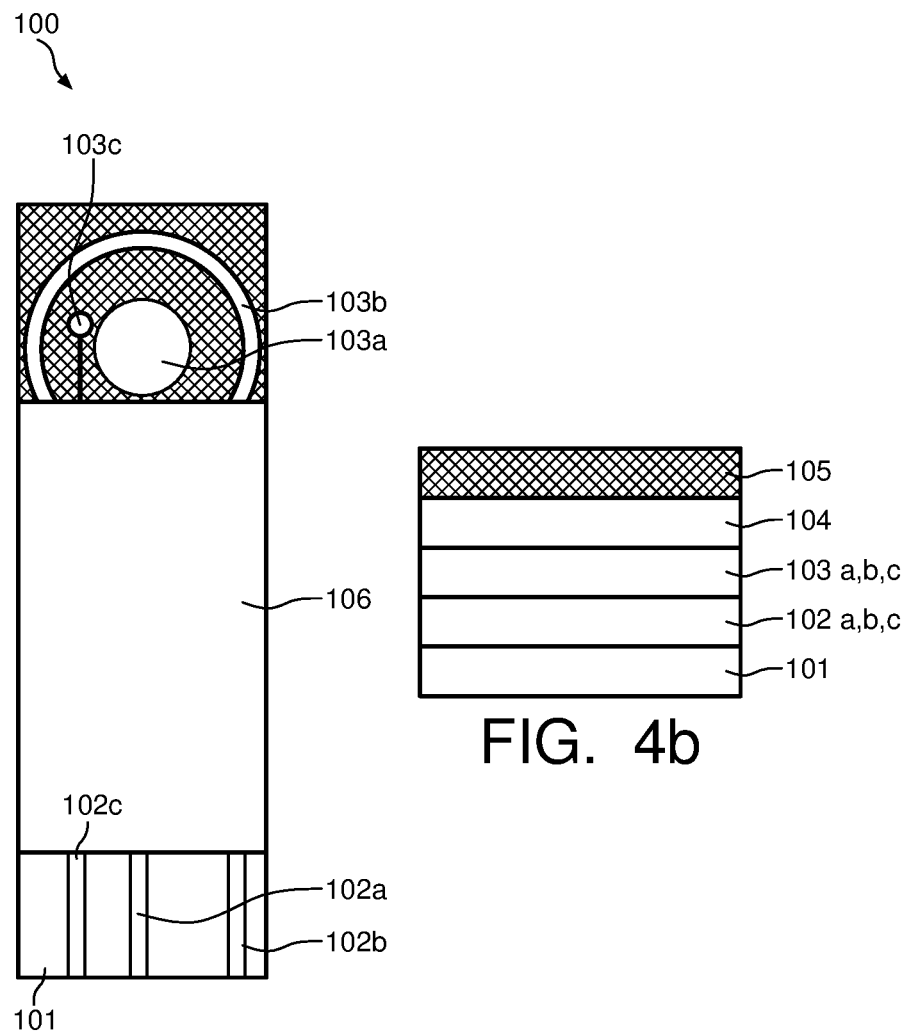
FIG. 4a
FIG. 4b
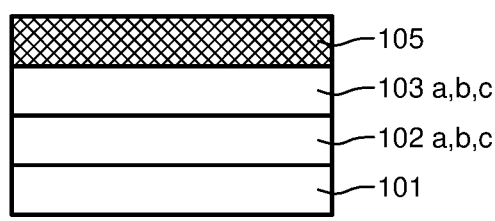
FIG. 4c
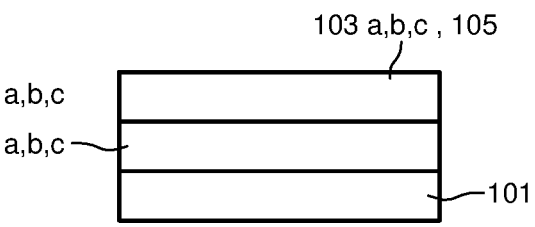
FIG. 4d

DEVICE AND METHOD FOR DETECTING CREATININE AND ALBUMIN TO CREATININE RATIO

FIELD OF INVENTION

The present invention relates to an electrochemically active device and method for detection and quantitative measurement of creatinine and albumin to creatinine ratio (ACR), electrochemically, in biological samples.

BACKGROUND OF THE INVENTION

Microalbuminuria is a well-established biomarker for an early detection of chronic kidney disease (CKD) in human subjects, where there is a moderate increase in the level of urine albumin. However, the accurate testing of microalbuminuria or moderately increased albuminuria, in a given urine sample, is generally affected by the concentration of the urine. As a result, urine albumin detection is performed in a 24-hour collated urine or timed collected urine samples for conducting the test for microalbuminuria. The 24-hour urine collection that is used for the determination of microalbuminuria is a cumbersome process and cannot be readily performed at a physician's place. Also, the chances of sample contamination are much higher in such places. In addition, the concentration (or dilution) of urine of a subject, also varies throughout the day, due to variations in the excretion levels of liquid, resulting in the variable concentrations of albumin in the urine sample. Due to this variation in urine concentrations, urine albumin measurement in random samples, may result in flagging of erroneous values.

Creatine phosphate (CP) is an organic compound of creatine and phosphoric acid found in the muscles of vertebrates, where its hydrolysis releases energy for muscular contraction. Creatine phosphate is high-energy compound that provides a small but rapidly mobilized reserve of high-energy phosphates that can be reversibly transferred to adenosine diphosphate (ADP) to maintain the intracellular level of adenosine triphosphate (ATP) during the first few minutes of intense muscular contraction. Creatine and creatine phosphate spontaneously cyclize at a constant rate to form creatinine, which is excreted in the urine. The amount of creatinine excreted is proportional to the total creatine phosphate content of the body and thus can be used to estimate muscle mass.

Creatinine, is a breakdown-product of creatinine phosphate in a muscle and is considered as the most important marker for the diagnosis of any abnormality in renal function, chronic kidney disease, thyroid and muscle dysfunctions, since the presence of these abnormalities and dysfunctions, in human subjects, causes abnormal variations in creatinine levels, in the corresponding blood and urine samples.

Creatinine is excreted at a constant rate into urine and its level in the urine is an indication of the amount of liquid being excreted as urine. Hence, the dilution of albumin in urine is well tracked by the dilution of creatinine in urine. This property of creatinine allows its measurement to be used as a corrective factor in urine albumin measurement in random urine samples. The American Diabetes Association and the International Society for Nephrology have mandated that ACR shall be a preferred marker for diagnosis of chronic kidney diseases.

For a human subject with normal functional kidneys, ACR of a random urine sample is less than 30 mg/g. However, if ACR is in the range of 30-300 mg/g, such a condition is referred to as microalbuminuria or a moderate increase in the level of urine albumin. Whereas, if ACR is greater than 300 mg/g, such a condition is referred to as macroalbuminuria or albuminuria.

Generally, albumin and creatinine are measured in a random urine samples and an albumin/creatinine ratio (ACR) is calculated. This may be done to more accurately determine how much albumin is escaping from the kidneys into the urine.

The most common devices and methods for detection and quantitative measurement of analytes, such as creatinine and albumin to creatinine ratio (ACR) in biological samples, are based on immunological techniques.

A potentiometric biosensor, based on creatinine iminohydrolase (E.C. 3.5.4.21), immobilized on chitosan membranes, which are coupled to a non-actin based ammonium ion selective electrode, is disclosed in *Analyst*, 2002, 127, 1069-1075 by Júlia M. C. S. Magãlhaes et al., for sensing creatinine.

Biosensors based on immobilized creatininase, creatinase and urease, using ion-sensitive field-effect transistor (ISFET), with a weak inversion at pH 6-8 and 37° C., are disclosed in *Sensors and Actuators B: Chemical Volume* 120, Issue 2, 10 Jan. 2007, Pages 732-735 by Bhusana Premanode et al.

CA2905780A1 discloses an immunochromatographic system, for measuring albumin and creatinine in a urine sample along with a reader, which detects signals from a test cassette, calculates, and displays the results for albumin concentration, creatinine concentration, and albumin/creatinine ratio.

WO2014/64633A1 discloses measurement of albumin and creatinine in urine and albumin to creatinine ratio, using immunochromatographic system.

US20140273269A1 discloses an immunochromatographic system for measuring albumin and creatinine in a urine sample and a reader that detects signals from the test cassette, calculates, and displays the results for albumin concentration, creatinine concentration, and albumin-creatinine ratio.

Point-of-care devices such as HemoCue, Axis shield's ACR and Siemens's DCA-Vantage are also known for use in the detection of creatinine and ACR.

However, all these known devices and methods are either based on immunological techniques or require a complex electrode modification, to measure these biological analytes.

Therefore, a need exists for a non-enzymatic and non-antibody-based receptors, which are more stable against the variations in ambient conditions for the electrochemical detection and quantification of bioanalytes related to urine creatinine, serum creatinine and urine albumin.

Objects of the Present Invention

Accordingly, it is an object of the present invention to provide a non-enzymatic and non-antibody-based electrochemically active, creatinine-binding device, to detect and measure quantitatively, creatinine in biological samples.

Another object of the present invention to provide a non-enzymatic and non-antibody-based electrochemically active, creatinine-binding and albumin-binding device, to detect and measure quantitatively, creatinine and albumin bioanalytes and to determine albumin to creatinine ratio (ACR), in biological samples.

Additional object of the present invention is to provide an electrochemically active and creatinine-binding device, for collection and retention of biological samples having creatinine bioanalyte.

A further object of the present invention is also to provide an electrochemically active, creatinine-binding and albumin-binding device, for collection and retention of biological samples, having creatinine and albumin bioanalytes.

Another object of the present invention is to provide a device holder, adapted to receive the electrochemically active, creatinine-binding and albumin-binding device.

It is also an object of the present invention is to provide a point-of-care biosensor, adapted to receive the electrochemically active creatinine-binding and albumin-binding device, for the detection and quantitative measurement of blood creatinine, urine creatinine and urine albumin to creatinine ratio (ACR), in biological samples of reduced volume, through a measurement of redox current, flowing through the electrochemically active device, on the application of an electric potential.

Yet another object of the present invention to provide a method for the detection and quantitative measurement of blood creatinine, urine creatinine and urine albumin to creatinine ratio (ACR), through an accurate measurement redox current flowing through the electrochemically active creatinine-binding and albumin-binding device.

These and other objects and features of the present invention will be apparent from the following detailed description taken with reference to the figures of the accompanying drawings.

BRIEF DESCRIPTION OF THE DRAWINGS

FIG. 4(a) is schematic top view illustration of the electrochemically active creatinine-binding device with a three-electrode arrangement, for the sensing of urine creatinine and blood creatinine bioanalytes.

FIG. 4(b) is a cross-sectional illustration of the electrochemically active creatinine-binding device, as shown in FIG. 4(a), where the receptor is arranged on the surface of a membrane.

FIG. 4(c) is a cross-sectional illustration of the electrochemically active creatinine-binding device, as shown in FIG. 4(a), where the receptor is arranged on the surface of an electrode.

FIG. 4(d) is a cross-sectional illustration of the electrochemically active creatinine-binding device, as shown in FIG. 4(a), where the electrode acts as a receptor.

SUMMARY OF THE PRESENT INVENTION

Figure 1:
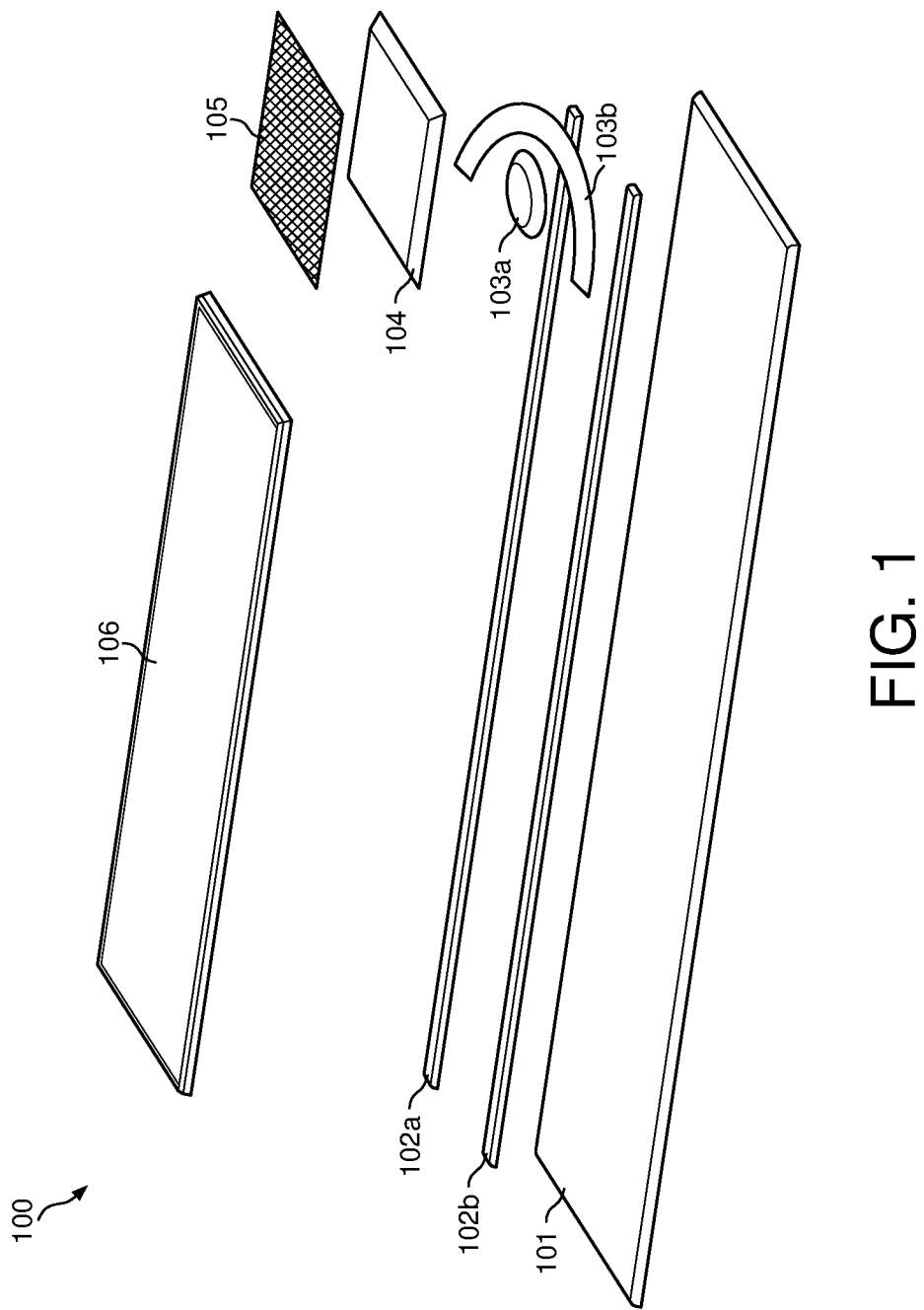
FIG. 1 is a schematic exploded illustration of the electrochemically active and creatinine-binding device, depicting a two-electrode arrangement, in accordance with an aspect of the present invention.

According to the present invention, there is provided an electrochemically active, creatinine-binding device, to detect and measure quantitatively, creatinine and in biological samples. The device of the present invention is also provided with a device to detect and measure quantitatively creatinine and albumin bioanalytes, simultaneously and to determine albumin to creatinine ratio (ACR). The present invention also provides an electrochemically active, creatinine-binding and albumin-binding device, for collection and retention of biological samples, having creatinine and albumin bioanalytes. In the present invention, a device holder is provided to receive the electrochemically active, creatinine-binding and albumin-binding device. The present invention further provides a point-of-care biosensor and method for measuring a bioanalyte in a biological sample. The device, point-of-care biosensor and the method of the present invention, facilitate quantitative measurement of creatinine and albumin bioanalytes in urine and blood samples, and albumin to creatinine ratio (ACR), in urine samples, electrochemically, by determining redox current values.

DETAILED DESCRIPTION OF THE INVENTION

Accordingly, the present invention provides an electrochemically active biosensor, for an accurate detection and quantitative measurement of creatinine and urine albumin to creatinine ratio (ACR), in reduced volumes of biological samples.

Creatinine forms the complexes with metal ions such as copper, iron, platinum and palladium. Accordingly, in present invention, an iron-creatinine complex chemistry is used for the electrochemical detection of creatinine in biological samples. For the present invention, the generally accepted reference range of values that are considered for urine creatinine is in the range of 40-300 mg/dl for male subjects and in the range of 37-250 mg/dl for female subjects. Similarly, the reference range of values for blood creatinine in the range of are 0.6-1.2 mg/dl for male subjects and 0.5-1.1 mg/dl for female subjects.

In an aspect of the present invention an electrochemically active device for collecting and retaining a biological sample is provided with electrically conductive tracks that are arranged on a substrate. At least a two-electrode member is connected to the conductive tracks and the electrode member is disposed to be in chemical contact with a creatinine-binding and electrochemically active receptor. The receptor, which is in chemical contact with the electrode member is arranged to receive and retain a desired biological sample, of reduced volume.

In an aspect of the present invention an electrochemically active device for collecting and retaining a biological sample is provided with electrically conductive tracks that are arranged on a substrate. At least a pair of three-electrode members are connected to the conductive tracks and the electrode members are disposed to be in chemical contact with a creatinine-binding, albumin-binding and electrochemically active receptors. The receptors, which are in chemical contact with the electrode members are arranged to receive and retain a desired biological sample, of reduced volume.

In another aspect of the present invention a holder for holding the electrochemically active device is provided with a housing having a device detection and signal conditioning circuitry. A Universal Serial Bus (USB) connector is arranged at one end of the housing and an electrically conductive port is arranged at the other end of the housing. The holder is adapted to receive the electrochemically active device through the electrically conductive port.

In yet another aspect of the present invention, a point-of-care biosensor for measuring a concentration of a bioanalyte in a biological sample is provided. The point-of-care biosensor comprises a housing with a display member and an interface, for inserting the electrochemically active and creatinine-binding device. The biosensor is provided with slots for inserting micro USB and a micro SD card. A digital controller is arranged in the housing and configured to apply a redox potential to the device, which is loaded with the biological sample having a creatinine bioanalyte. The digital controller is also configured to display or use the concentration of the creatinine bioanalyte by measuring a corresponding redox current and linearly matching it to the creatinine concentration.

In further aspect of the present invention a method is provided for measuring a concentration of a bioanalyte in a reduced volume of a biological sample by applying a redox potential to at least a two-electrode member having an electrochemically active and a creatinine binding receptor loaded with a reduced volume of a biological sample having creatinine bioanalyte and determining a concentration of the creatinine bioanalyte in the bio-sample by linearly matching with a corresponding redox current.

In yet another aspect of the present invention a method is provided for quantitative measurement of creatinine and albumin to creatinine ratio (ACR), electrochemically, in biological samples.

Now, the preferred embodiments of the invention are described by referring to the figures of the accompanying drawings. FIG. 1 illustrates an electrochemically active device that is adapted to collect and retain a desired biological sample, which is urine or blood, for subsequent measurement of creatinine analyte present in the biological sample.

The device 100 as shown in FIG. 1 is provided with a substrate 101, to act as a base on which other constituents of the device are constructed. The substrate 101, in this embodiment is exemplarily shown as an elongated rectangular structure. However, it is understood here that the substrate 101 can take other shapes such as square, circular etc., and particularly depends on the shape and configuration of a biosensor that is adapted to hold the device 100. The substrate 101 can be made of any suitable rigid or flexible material that is suitable for the incorporation of patterned electrodes. For instance, materials such as polyvinylchloride (PVC), polyethylene terephthalate (PET), polymethylmethacrylate (PMMA), epoxy fiber composites, polyamides composites or a paper can be used as preferred materials for the substrate 101.

Whereas, the preferred rigid materials for the substrate 101 can be ceramic, glass or any other like materials. In any case, the selection of suitable material for the substrate 101 is made, to ensure that the substrate 101 can provide not only a desirable strength and flexibility but also can act as a desirable electrical insulator. Advantageously, in the present invention, the substrate 101 is hydrophilic in nature, to prevent percolation of the biological sample, whenever the sample comes in physical contact with the substrate 101. The surface of the substrate 101 is generally provided with a smooth texture. However, the substrate 101 can also be provided with a rough surface and/or with cavities or wells. The edges of the substrate 101 carry suitable profiles, such as tapered or curved, to facilitate an easy ingress into and egress out of the biosensor as here-in-after described.

Conductive tracks 102a and 102b are arranged on the substrate 101. The conductive tracks 102a and 102b are formed by using any patterning method such as screen printing, lithography, thermal evaporation, sputtering, laser patterning, preferably screen-printing. In an exemplary aspect, in FIG. 1, pair of conductive tracks 102a and 102b are formed for implementation. However, the required number of conductive tracks can be suitably increased or varied. The routing of the conductive tracks 102a and 102b are exemplarily shown as straight tracks in FIG. 1. Other suitable configurations for the conducting tracks such as polygons can be used. The material for the conductive tracks 102a and 102b can be an electrically conductive material such as copper, aluminum, gold, silver, platinum, carbon, or any other suitable electrically conducting material or alloys of these materials. The material for the conducting tracks 102a and 102b can also be electrochemically active such as gold, platinum, mercury, carbon, glassy carbon and graphite. The conducting tracks 102a and 102b are used to establish an electrical connection with the device/biosensor of the present invention.

A two-electrode member 103a and 103b are electrically connected to the conducting tracks 102a and 102b respectively, as shown in FIG. 1. The electrodes 103a and 103b are overlaid on the conducting tracks 102a and 102b and arranged at the terminal ends of the conducting tracks 102a and 102b, so as to form a layer above the conducting tracks 102a and 102b, as shown in FIG. 1. The material for the electrodes 103a and 103b is selected from metals, which are electrochemically active, such as gold, platinum, mercury, carbon, glassy carbon and graphite. The alloys of these metals can also be suitably adapted for use. In the arrangement of electrodes as shown in FIG. 1, the electrode 103a acts as a working electrode and the electrode 103b functions as a counter electrode.

A membrane 104 is arranged on the electrodes 103a and 103b as shown in FIG. 1, which acts as base member for the integration of a receptor as hereinafter described. The material for the membrane 104 can be polymer, cellulose, nitrocellulose, nylon, cotton fabric, filter paper etc.

The device 100 of present invention is used for the detection and quantitative measurement of creatinine bioanalyte in biological samples of urine and blood. Accordingly, in the present invention a creatinine-binding and an electrochemically active receptor 105 is disposed to be in chemical contact the electrodes 103a and 103b and the creatinine bioanalyte of the biological sample through the membrane 104. The receptor 105, in this preferred embodiment, is an electrochemically active substance, advantageously formed as a substance.

The electrochemically active substance that is used as a receptor 105 to detect creatinine in urine biological and serum samples, is a creatinine-binding and electrochemically active metal, preferably iron ($Fe^{+2}$ and $Fe^{+3}$), palladium ($Pd^{+2}$), platinum ($Pt^{+2}$) and metal halide ions thereof, preferably chloride and sulphate ions.

In yet another aspect of the present invention, the electrochemically active substance that is used as a receptor 105 to detect creatinine in urine biological and serum samples, is a creatinine-binding and electrochemically active substance, is a combination of methylene blue (MB) and electrochemically active metal, preferably, iron ($Fe^{+2}$ and $Fe^{+3}$), palladium ($Pd^{+2}$), platinum ($Pt^{+2}$) and metal halide ions thereof, preferably chloride and sulphate ions.

Advantageously, the initiation of chemical contact of the receptor 105 with the electrodes 103a and 103b is performed by preparing a solution of the receptor 105 and the prepared solution is dispensed on the electrodes and/or membrane and dried to form a solid chemical layer on the electrodes 103a and 103b and membrane 104.

Alternately, the receptor solution is pre-mixed with the biological sample and a reduced volume of the pre-mixed solution is dispensed on the electrodes 103b and 103b or on the membrane 104.

The initiation of chemical contact of the receptor 105 with the electrodes 103a and 103b can also be performed by preparing a receptor solution separately and dispensing the prepared solution on the electrode/membrane. Thereafter, the desired biological sample having creatinine bioanalyte is applied on the electrodes.

A passivation layer 106 is arranged to cover the conductive tracks as shown in FIG. 1. The passivation layer 106 is used to provide protection for the conductive elements of the device and to precisely define the electrode region.

Therefore, as shown in FIG. 1, the electrochemically active device for collecting and retaining a biological sample, comprises, at least a two-electrode members 103a and 103b connected to conductive tracks 102a and 102b. The creatinine-binding and an electrochemically active receptor 105 is arranged to be in chemical contact with the at least two-electrode members 103a and 103b and with a creatinine bioanalyte of a biological sample, which is urine or blood.

It is also within the purview of this invention to increase the number of electrodes for the detection of bioanalytes. For instance, the number of pairs of two-electrode members, as shown in FIG. 1 can be suitably increased, for sensing the desired bioanalytes and also to increase the sensitivity of the device. Use of additional electrode members imparts an enhanced accuracy to the measurement of the desired bioanalyte concentrations by providing the additional electrodes and reference electrodes.

Figure 2:
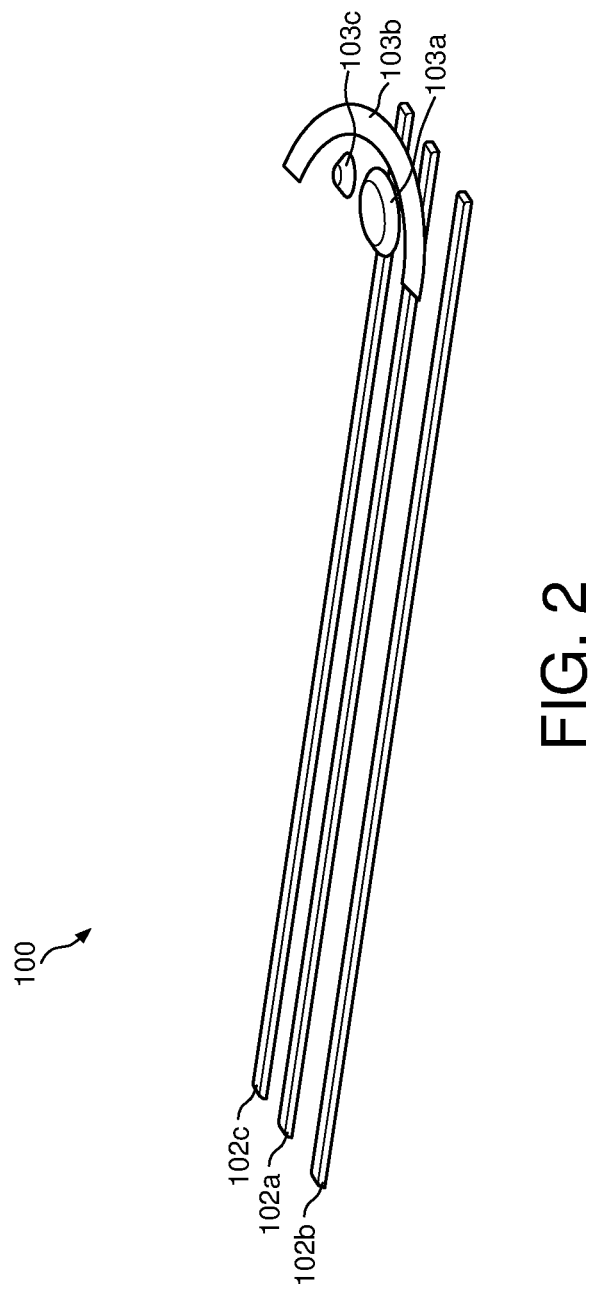
FIG. 2 is a schematic exploded illustration of the electrochemically active and creatinine-binding device, depicting a three-electrode arrangement, in accordance with another aspect of the present invention.

In yet another aspect of the present invention, as shown in FIG. 2, an arrangement of three-electrode members 103a, 103b and 103c is implemented in conjunction with a receptor (as shown in FIG. 1), where the electrodes 103a, 103b and 103c are connected to the conducting tracks 102a, 102b and 102c respectively, to receive and retain a biological sample. The increased number of electrodes facilitates the detection of a single bio-analyte in the biological sample with an increased accuracy. In this implementation the electrode 103c acts as a reference electrode. The preferred material for the reference electrode 103c is silver (Ag), a silver chloride (AgCl), silver/silver chloride (Ag/AgCl) or saturated calomel, where the potential of the electrodes does not change with time.

Figure 3A:
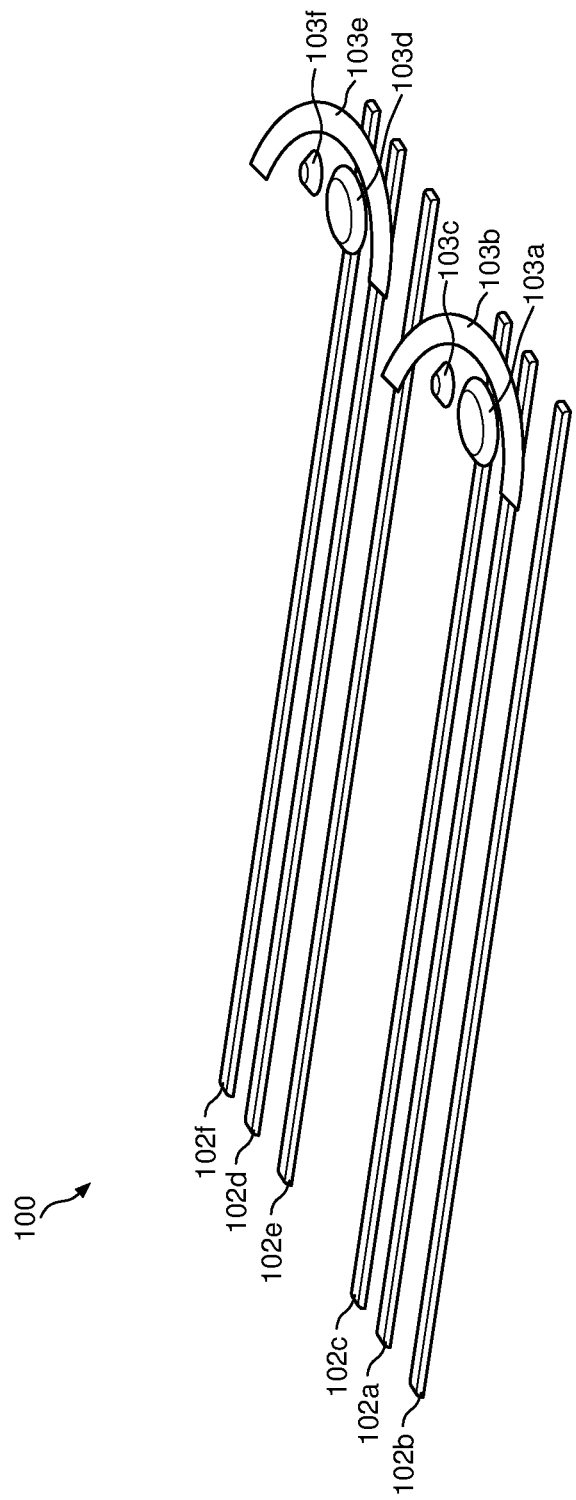
FIG. 3(a) is a schematic exploded illustration of two pairs of three-electrode arrangement, of the electrochemically active creatinine and albumin-binding device, in accordance with yet another aspect of the present invention.
Figure 3B:
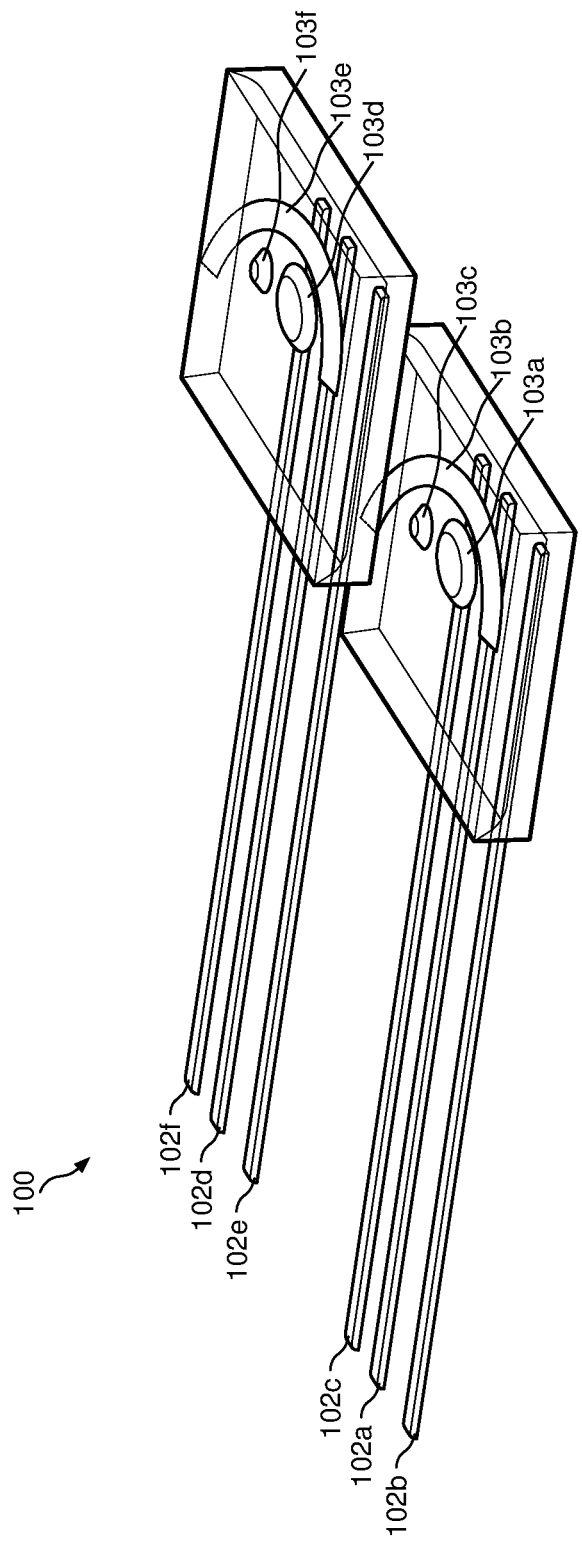
FIG. 3(b) is a schematic exploded illustration of two pairs of three-electrode arrangement with trays, of the electrochemically active creatinine and albumin-binding device, in accordance with yet another aspect of the present invention.

In yet another aspect of the present invention, two sets of three-electrodes 103a, 103b, 103c, 103d, 103e and 103f are arranged on the conducting tracks 102a, 102b, 102c, 102d, 102e and 102f, as shown in FIG. 3(a) and are adapted for use to measure preferably, albumin to creatinine ratio (ACR), in urine samples, after measuring, independently, the values of urine albumin and creatinine from the respective electrodes. In this arrangement, the electrodes 103c and 103f act as reference electrodes. In the event, the desired biological samples are blood and urine, shielded wells or trays are arranged on the electrodes 103a, 103b, 103c, 103d, 103e and 103f, to demarcate the two different sensing areas, as shown in FIG. 3(b) and to facilitate an independent sensing of the biological samples. Accordingly, in this arrangement, two separate receptors are provided in conjunction with each set of the electrodes, to receive the biological samples, to sense albumin and creatinine and to measure the albumin to creatinine ratio (ACR). In addition, if deemed necessary, physical partitions may be provided to separate the electrodes.

It is understood here that two sets of two-electrode arrangement can also be suitably adapted for use in place of two sets of three-electrode arrangement, for detecting and measuring separate bioanalytes.

In this aspect, it is understood that the total number of the sets of three-electrode arrangement can be suitably increased, for detecting the desired bioanalytes and also to increase the sensitivity of the device. In special cases where the biomarkers are more than two then multiple set of three electrodes can be suitably adopted for use.

Now, the preferred embodiments of the receptor, which is electrochemically active and binds creatinine and albumin present in urine and blood samples are now described, by particularly referring to FIG. 4(a) to FIG. 4(d), which are illustrative representations of the device 100 having a three-electrode arrangement.

Accordingly, FIG. 4(a) illustrates the arrangement of the electrodes 103a, 103b and 103c, on the substrate 101, of the electrochemically active and creatinine-binding device 100, where the electrodes are connected to the conducting tracks 102a, 102b and 102c respectively. The device 100 is disposed to receive and retain a biological sample (urine/blood).

FIG. 4(b), which is a corresponding cross-sectional view of the device 100 as shown in FIG. 4(a), illustrates the substrate 101 on the surface of which conducting tracks 102a, 102b and 102c are arranged. A three-electrode arrangement in the form of a working electrode 103a, a counter electrode 103b and a reference electrode 103c, is connected to the conducting tracks 102a, 102b and 102c. The membrane 104 is arranged on surface of the electrodes 103a, 103b and 103 and the receptor layer 105 is arranged on the surface of the membrane 104.

Now turning to FIG. 4(c), the electrochemically active and creatinine-binding device of the present invention is illustrated, where the conducting tracks 102a, 102b, 102c are arranged on the substrate 101. A three-electrode arrangement in the form of a working electrode 103a, a counter electrode 103b and a reference electrode 103c is connected to the conducting tracks 102a, 102b and 102c. The receptor 105 is arranged on surface of the electrodes 103a, 103b and 103c.

FIG. 4(d), which is a corresponding cross-sectional view, illustrates the arrangement of the electrochemically active and creatinine-binding device of the present invention where the substrate 101 on the surface of which conducting tracks 102a, 102b and 102c are arranged. A three-electrode arrangement in the form of a working electrode 103a, a counter electrode 103b and a reference electrode 103c, is connected to the conducting tracks 102a, 102b and 102c, where the electrodes are treated with the receptor 105.

The electrochemically active and creatinine-binding device, as illustrated in FIG. 4(a) (b), (c) and (d) is used to measure creatinine bioanalyte in urine and blood samples. The receptor 105 for the three-electrode arrangement is the one as described in the aforementioned embodiments.

Figure 5A:
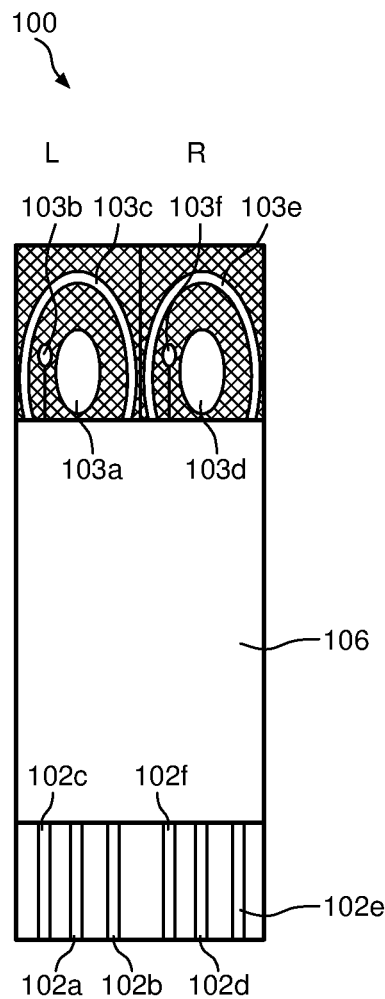
FIG. 5(a) is schematic top view illustration of the electrochemically active creatinine and albumin-binding device with two sets of a three-electrode arrangement for quantitative measurement of urine creatinine and urine albumin.

Now, by referring particularly to FIG. 5(a), (b), (c), (d), (e), (f) and (g), the preferred embodiments of the device 100 for measuring the albumin to creatinine ratio (ACR) in urine samples, are described. In this aspect, for sake of clarity and illustration, the two pairs of three-electrode systems of the device 100 are shown with left (L) and right portions (R), where the left portion (L) is adapted to collect urine sample for creatinine measurement and the corresponding right portion (R) is used for collecting urine sample for albumin measurement.

Accordingly, FIG. 5(a) illustrates the electrochemically active and creatinine-binding and albumin-binding device, for the measurement of urine albumin to creatinine ratio (ACR), subsequent to the measuring of urine albumin and creatinine separately, in the biological samples. In this aspect, two pairs electrodes 103a, 103b, 103c (left portion) and 103d, 103e, 103f (right portion) are arranged on the substrate 101, where the electrodes are connected to the conducting tracks 102a, 102b, 102c and 102d, 102e, 102f respectively, to receive and retain a biological sample.

Figure 5B:
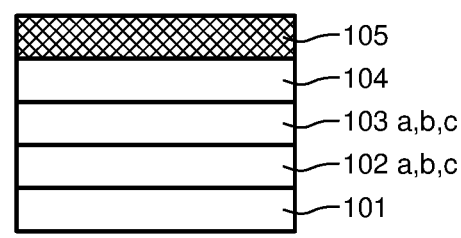
FIG. 5(b) is a cross-sectional illustration of the electrochemically active, creatinine-binding and albumin-binding device, as shown in FIG. 5(a), where the receptor is arranged on one set (figuratively on the left set) of three electrodes and on the surface of the membrane for urine albumin detection.

FIG. 5(b), which is a corresponding cross-sectional view of FIG. 5(a), illustrates the substrate 101 on the surface of which conducting tracks 102a, 102b and 102c are arranged in the left half portion of the substrate 101. A three-electrode arrangement is provided in the left half portion of the substrate 101, in the form of a working electrode 103a, a counter electrode 103b and a reference electrode 103c and is connected to the conducting tracks 102a, 102b and 102c. The membrane 104 is arranged on surface of the electrodes 103a, 103b and 103c along with the receptor layer 105, which is arranged on the surface of the membrane 104. The receptor 105 for the three-electrode arrangement is the one as described in the aforementioned embodiments.

Figure 5C:
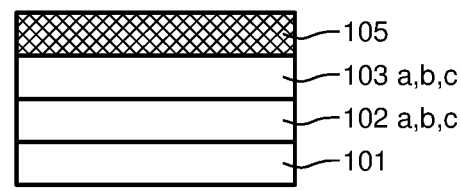
FIG. 5(c) is a cross-sectional illustration of the electrochemically active, creatinine-binding and albumin-binding device, as shown in FIG. 5(a), where the receptor is arranged on one set of three electrodes and on the surface of the electrode for urine albumin detection.

FIG. 5(c), which is a corresponding cross-sectional view of FIG. 5(a), illustrates the substrate 101 on the surface of which conducting tracks 102a, 102b and 102c are arranged in the left half portion of the substrate 101. A three-electrode arrangement is provided in the left half portion of the substrate 101 in the form of a working electrode 103a, counter electrode 103b and a reference electrode 103c and is connected to the conducting tracks 102a, 102b and 102c along with the receptor 105, which is arranged on surface of the electrodes 103a, 103b and 103c. The receptor 105 for the three-electrode arrangement is the one as described in the aforementioned embodiments.

Figure 5D:
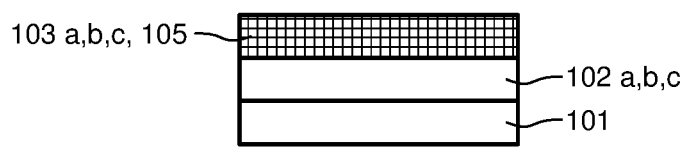
FIG. 5(d) is a cross-sectional illustration of the electrochemically active, creatinine-binding and albumin-binding device, as shown in FIG. 5(a), where one set of three electrodes acts as a receptor for urine albumin detection.

FIG. 5(d), which is a corresponding cross-sectional view of FIG. 5(a), illustrates the substrate 101 on the surface of which the conducting tracks 102a, 102b and 102c are arranged in the left half portion of the substrate 101. A three-electrode arrangement is provided in the left half portion of the substrate 101 in the form of a working electrode 103a, a counter electrode 103b and a reference electrode 103c and is connected to the conducting tracks 102a, 102b and 102c, where the electrodes are treated with the receptor 105.

Figure 5E:
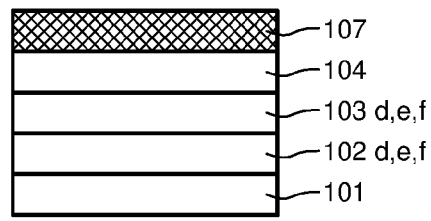
FIG. 5(e) is a cross-sectional illustration of the electrochemically active creatinine and albumin binding device, as shown in FIG. 5(a), where the receptor is arranged on other set of three electrodes and on the surface of the membrane for urine creatinine detection.

FIG. 5(e), illustrates a substrate 101 on the surface of which conducting tracks 102d, 102e and 102f are arranged in the right half portion of the substrate 101. A three-electrode arrangement is provided in the right half portion of the substrate 101 in the form of a working electrode 103d, a counter electrode 103e and a reference electrode 103f and is connected to the conducting tracks 102d, 102e and 102f. The membrane 104 is arranged on surface of the electrodes 103d, 103e and 103f. The receptor layer 107 is arranged on the surface of the membrane 104.

The receptor 107, in this preferred embodiment, is advantageously shown as a layer of electrochemically active substance. The constituent elements of receptor 107 are as described in the Applicant's co-pending PCT Application No. PCT/IB2015/056619, the contents of which are incorporated herein by reference. Accordingly, the urine albumin-binding receptor 107 is at least an organic, inorganic or a metal porphyrin substance, preferably, hemin, hematin, alkaline hematin, copper chloride ($CuCl_2$) and a salt of copper (Cu(II)).

In yet another aspect of the present invention, the urine albumin-binding receptor 107 is a combination of methylene blue (MB) and one of hemin, hematin, alkaline hemin, alkaline hematin, copper chloride ($CuCl_2$) or a salt of copper (Cu(II)).

In yet another aspect of the present invention, the membrane 104, as shown in FIG. 5(e) is treated with urine albumin-binding receptor, said receptor is at least an organic, inorganic, metal porphyrin substance, preferably, hemin, hematin, alkaline hematin, copper chloride ($CuCl_2$) and a salt of copper (Cu(II)).

In yet another aspect of the present invention, the membrane 104, as shown in FIG. 5(e) is treated with urine albumin-binding receptor is a combination of methylene blue (MB) and one of organic, inorganic, metal porphyrin substance, preferably, hemin, hematin, alkaline hematin, copper chloride ($CuCl_2$) and a salt of copper (Cu(II)).

Accordingly, the electrochemically active and albumin-binding substance that is used as a receptor 107, to detect urine albumin in a urine biological sample and serum albumin (SA) in a biological blood sample, is at least an organic, inorganic or a metal porphyrin substance, preferably, hemin, hematin, alkaline hematin, copper chloride ($CuCl_2$) and a salt of copper (Cu(II)).

In yet another aspect of the present invention, said urine albumin-binding receptor 107 is a combination of methylene blue (MB) and one of hemin, hematin, alkaline hemin, alkaline hematin, copper chloride ($CuCl_2$) or a salt of copper (Cu(II)).

Figure 5F:
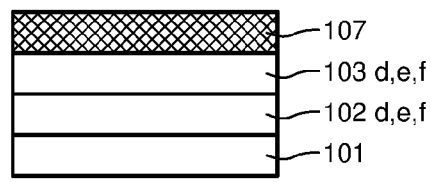
FIG. 5(f) is a cross-sectional illustration of the electrochemically active and albumin-binding device, as shown in FIG. 5(a), where the receptor is arranged on other set of three electrodes and on the surface of the electrode for urine creatinine detection.

FIG. 5(f), which is a corresponding cross-sectional view depicting a substrate 101 on the surface of which conducting tracks 102d, 102e, 102f are arranged in the right half portion of the substrate 101. A three-electrode arrangement in the right half portion of the substrate 101 in the form of a working electrode 103d, counter electrode 103e and reference electrode 103f, which are connected to the conducting tracks 102d, 102e, 102f. The receptor 107 is arranged on surface of the electrodes 103d, 103e and 103f.

Figure 5G:
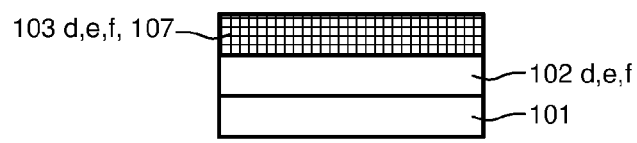
FIG. 5(g) is a cross-sectional illustration of the electrochemically active, creatinine-binding and albumin-binding device, as shown in FIG. 5(a), where other set of three electrodes, acts as a receptor for urine creatinine detection.

FIG. 5(g), which is a corresponding cross-sectional view depicting a substrate 101 on the surface of which the conducting tracks 102a, 102b, 102c are arranged in the right half portion of the substrate 101. A 3-electrode arrangement in the right half portion of the substrate 101 with a working electrode 103a, counter electrode 103b and reference electrode 103c is connected to the conducting tracks 102a, 102b, 102c, where the electrodes are treated with the receptor 107. The embodiments as shown in FIG. 5(a), (b), (c), (d), (e), (f) and (g) are used to measure the albumin to creatinine ratio (ACR) in urine samples.

Therefore, the electrochemically active device of the present invention for collecting and retaining a biological sample, comprises at least two pairs of conductive tracks 102a, 102b, 102c and 102d, 102e, 102f are disposed on the substrate. At least two pairs of electrode members 103a, 103b, 103c and 103d, 103e, 103f are connected to the conductive tracks 102a, 102b, 102c and 102d, 102e, 102f, respectively. The urine albumin-binding and creatinine-binding receptors 105 and 107 are arranged to be in chemical contact with the at least two pairs of electrode members 103a, 103b, 103c and 103d, 103e, 103f and with urine albumin and urine creatinine bioanalytes of the biological sample. Accordingly, in this preferred embodiment, an arrangement of device 100 is provided, where the same device can be used for sensing urine albumin and urine creatinine, by means two respective receptors 105 and 107, for eventual measurement of ACR from the biological sample.

It is appreciated here that the receptors, which are creatinine-binding and albumin binding are described in conjunction with a pair and two sets of three-electrode arrangement of the device of the present invention. Accordingly, these embodiments can also be implemented in conjunction with two-electrode and three-electrode arrangements of the device as illustrated in FIG. 1 and FIG. 2.

In yet another aspect of the present invention, the device 100 is arranged in a housing, where the housing is a cartridge or a cassette.

Figure 6:
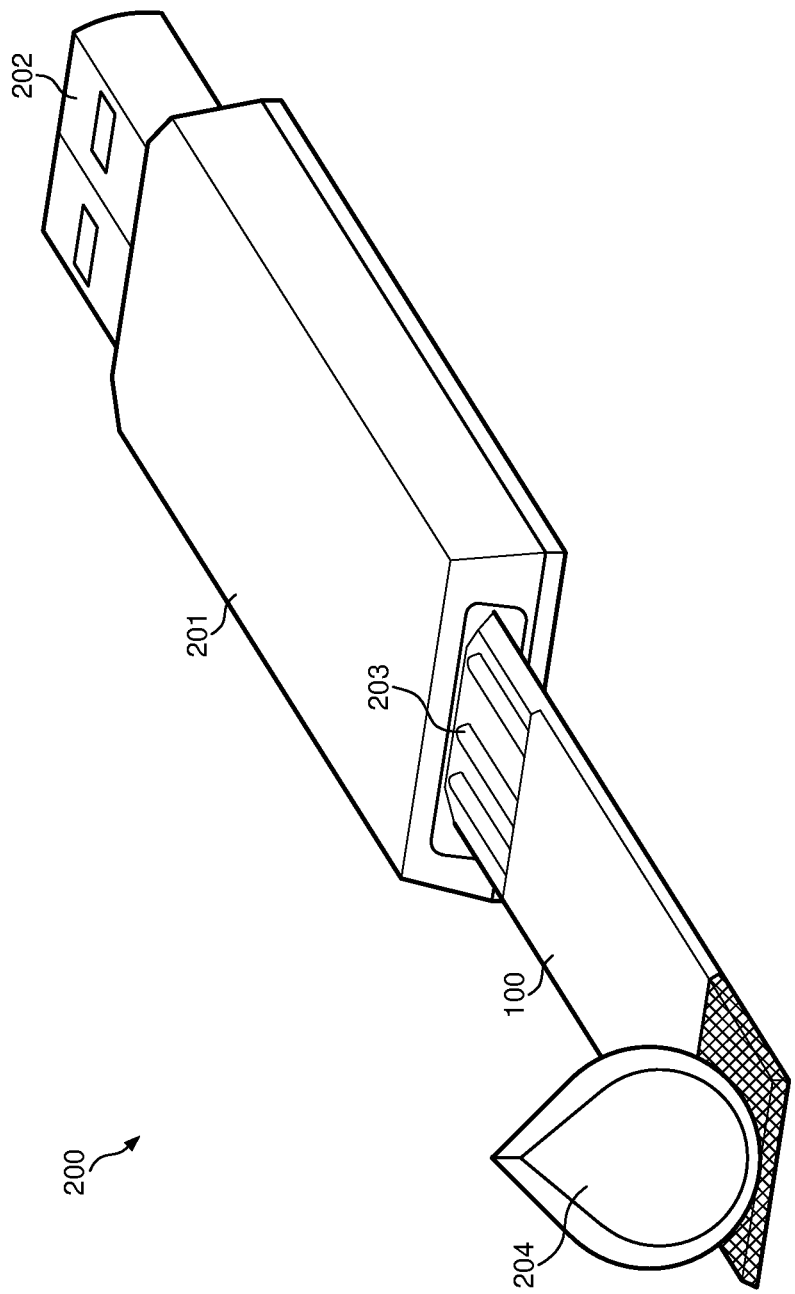
FIG. 6 is a perspective illustration of the device holder holding the device of the present invention.

In yet another aspect of the present invention, constituent elements of a device holder 200, to hold the device 100 and to use for detecting a bioanalyte in a bio-sample are now described, by referring particularly to FIG. 6. The device holder 200 comprises a housing 201 with a device detection and signal conditioning circuit and the housing 201 is adapted to connect to a digital processor and a display member. The signal conditioning circuitry applies redox current across the conductive lines of working and reference electrodes of the device and simultaneously measures the redox current for further analysis of concentration of the desired bioanalytes. A device insertion port 203 is provided in the housing 201. The device 100, which is adapted to fit into a device insertion port 203, includes a substrate with at least a two-electrode member along with a creatinine-binding and an electrochemically active receptor, connected to the housing 301, and the creatinine-binding and an electrochemically active receptor is configured to receive a biological sample 204. A USB plug or connector 202 is connected to the housing 201 as shown in FIG. 6. The device holder 200 is used to collect and retain the biological sample 204 for subsequent testing. The device holder 200 is also provided with device detection, signal conditioning and data acquisition features, to identify the type of bioanalyte that is stored on the device 100. The device holder 200 enables a user to insert the holder 200 into a biosensor and collect the biological sample for measurement.

Accordingly, the device holder 200 for holding a creatinine-binding and electrochemically active device 100, comprises a device detection and signal conditioning means disposed in a housing 201. A USB connector 202 disposed at one end of the housing and an electrically conductive port disposed at the other end of said housing. The electrochemically-active device 100 is disposed to connect to said housing 201 through the electrically conductive port 203, for collecting and retaining a biological sample with creatinine bioanalyte. The device 100 is provided with at least a two-electrode member, which is connected to the conductive tracks of the substrate and a creatinine-binding and an electrochemically active receptor, disposed to be in chemical contact with the at least two-electrode member and with the creatinine bioanalyte of the biological sample.

In further aspect of the present invention constituent elements of a holder 200 for holding a creatinine, urine albumin-binding and electrochemically active device are described. The device detection and signal conditioning means disposed in a housing 201. The USB connector 202 is disposed at one end of the housing 201 and an electrically conductive port 203 is disposed at the other end of said housing 201. An electrochemically-active device is disposed to connect to the housing through the electrically conductive port for collecting and retaining a biological sample with creatinine and urine albumin bioanalytes. The device 100 is provided with at least two sets of three-electrode members connected to the conductive tracks of the substrate and urine albumin-binding and creatinine-binding receptors. The receptors are disposed to be in chemical contact with at least the two sets of three-electrode members and with urine albumin and urine creatinine bioanalytes of the biological sample.

Figure 7A:
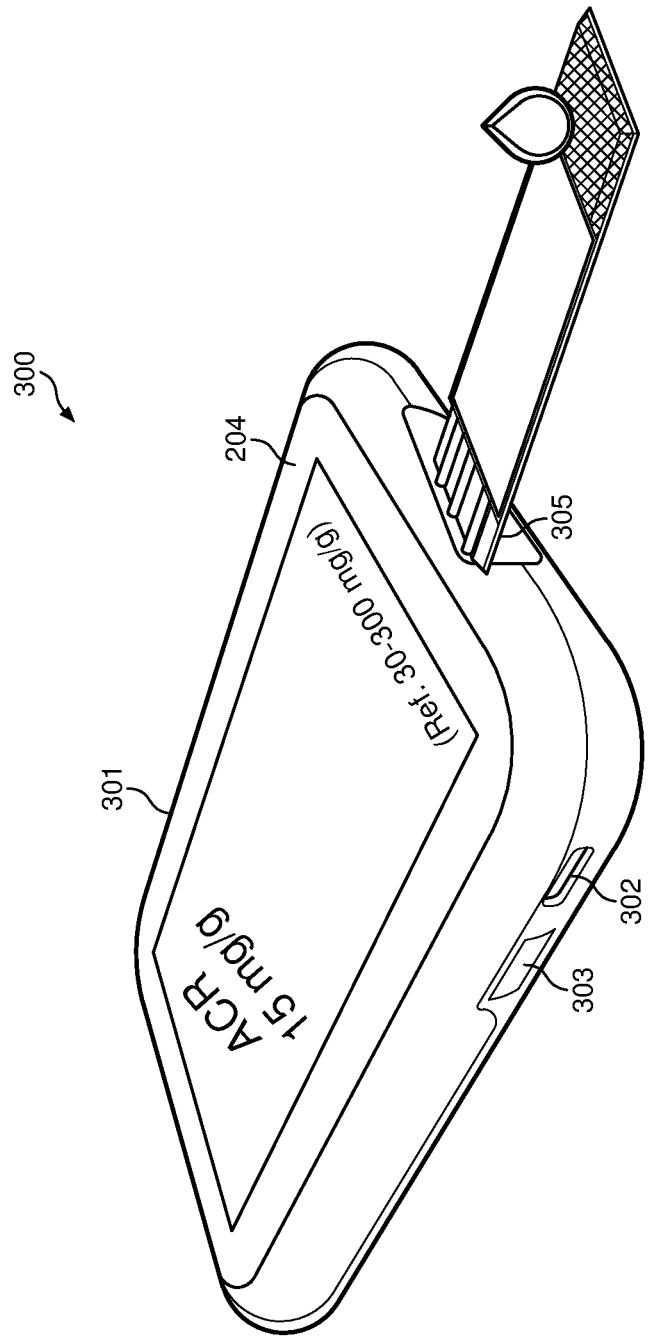
FIG. 7(a) is a perspective illustration of point-of-care biosensor holding the device of the present invention.
Figure 7B:
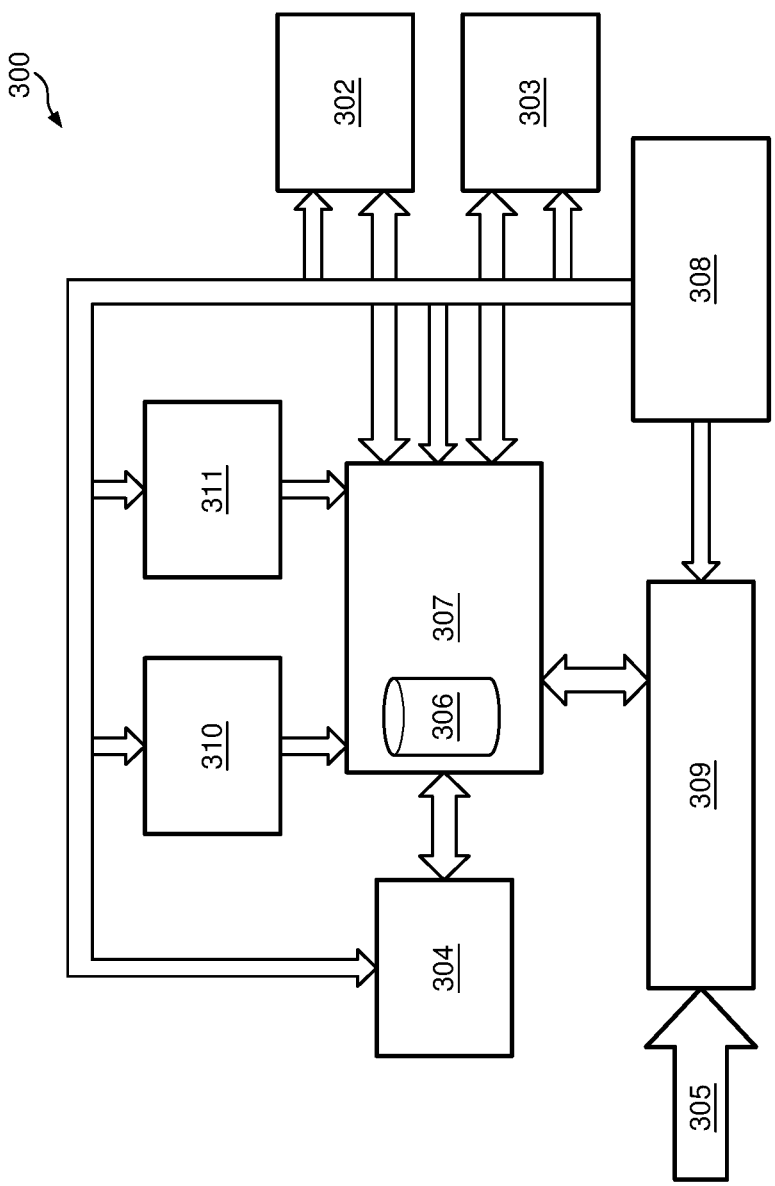
FIG. 7(b) is an illustrative schematic depiction of broad internal electronic architecture of the point-of-care biosensor.

The preferred embodiments of a point-of-care biosensor 300 for sensing a bioanalyte in a biological sample, by using the device 100 of the present invention are now described by particularly referring to FIG. 7(*a*). The point-of-care biosensor 300, is a computing device such as portable computer, smart phone etc., having a digital processor. The biosensor 300 comprises a housing 301. The housing 301 is equipped to connect a micro USB and micro SD card through the ports 302 and 303 of the housing 300. The micro USB 302 is used to charge the biosensor 300 and micro SD card is used as a storage device. The housing 301 is also provided with display member 304, which can be an LCD, LED, OLED, OMLED, TFT or any other such display devices, including touch-sensitive devices. A device insertion port 305 is provided in the housing 301. The device insertion port 305 is provided with a metallic contact to engage with the device 100, electrically. In other words, the insertion port 305 is provided to receive the device 100, through the electrode members of the device 100. The point-of-care biosensor 300 is provided to facilitate a user to use the device 100, in a simple way, along with the point-of-care biosensor 300. The device 100 is initially inserted into the loaded point-of-care biosensor 300 and loaded with a selected biological sample, in reduced volume, in the range of 1-300 µL, which entails a minimum invasive means in collecting the biological sample 304. The user is also at liberty to use the biosensor 300 at room temperature and without concerning about other environmental factors such as humidity, temperature variation and storage conditions. The user by using the biosensor 300 is able to measure the concentration levels of the desired bioanalytes, in a substantially shorter period of time, since the bioanalyte binds the receptor, instantaneously. The user is provided with an instantaneous and accurate display of the concentration of the bioanalyte on the display member 306, since the inherent binding nature of bioanalyte is used in the biosensor 300 to measure the concentration levels. By using the biosensor 300 of the present invention, the user is enabled to use the biosensor without a need for active preparation of the biological sample before it is tested.

Accordingly, the point-of-care biosensor for measuring a concentration of a creatinine bioanalyte in a biological sample is provided. The electrochemically-active device is disposed to connect to the housing through the electrically conductive port for collecting and retaining the biological sample. The device is provided with at least a two-electrode member connected to the conductive tracks of the substrate and to the creatinine-binding and electrochemically active receptor. The receptor is disposed to be in chemical contact with the at least two-electrode member and with the creatinine bioanalyte of the biological sample. The digital controller is disposed in the housing and configured to measure redox current from a redox potential applied to the device to retrieve and render creatinine bioanalyte concentration, by linearly matching the concentrations of creatinine.

In yet another aspect of the present invention, a point-of-care biosensor for measuring albumin to creatinine ratio (ACR) in a biological sample is provided. An electrochemically-active device is disposed to connect to the housing through the electrically conductive port for collecting and retaining the biological sample. The device is provided with at least two sets of three-electrode members connected to conductive tracks of a substrate. The urine albumin-binding and creatinine-binding receptors are disposed to be in chemical contact with the least two sets of three-electrode members and with urine albumin and urine creatinine bioanalytes of the biological sample. The digital controller that is disposed in the housing is configured to measure redox currents of urine creatinine and urine albumin from a redox potential applied to the device. The digital controller is also disposed to calculate and render albumin to creatinine ratio (ACR) in the urine sample by linearly matching the concentrations of urine creatinine and urine albumin with corresponding redox currents.

Now, particularly referring to FIG. 7(*b*), features of a broad internal electronic hardware architecture of the biosensor 300 are described. A database member 306 is provided in the housing 301 as shown in FIG. 7(*a*), to store standard values of redox current and bioanalyte concentration of urine creatinine, serum creatinine, urine albumin, present in the biological samples. The database 306 also incorporates the data pertaining to historical and current data of concentrations of the bioanalytes. The executables that are required to perform the various functions of the biosensor 300 are stored on a medium of the biosensor 300. A digital controller 307 is provided in the housing 301 and connected to the database member 306 and configured to apply a redox potential to at least a two-electrode member having an electrochemically active and a creatinine-binding receptor with a biological sample having creatinine bioanalyte and to measure the corresponding redox current. The digital controller 307 is arranged to measure a redox current of the creatinine bioanalyte by linearly matching with the value of concentration and display the value of measured concentration of the creatinine bioanalyte.

The database member 306 is stored with standard values of creatinine bioanalyte concentrations along with reciprocal redox currents.

A power supply to the biosensor 300 is regulated by a power supply unit 308, which is connected to the biosensor 300. The power supply unit 308 includes both online and offline rechargeable battery with charging circuitry. A signal conditioning and device detection unit 309 is connected to the microcontroller 307 to detect the presence of the device 100 in the biosensor 300 and to apply the redox potential to the electrodes and measuring the redox current from the selected biological sample. Signal conditioning circuitry of the signal conditioning and device detection unit 309 applies redox current across the conductive lines of working and reference electrodes of the biosensor 300 and simultaneously measures the redox current for further analysis of concentration of the desired bioanalytes.

Humidity and temperature sensors 310 and 311 are arranged in the housing 301. Once the measurement of the concentration levels of the bioanalyte is completed by the microcontroller 307, the concentration levels are displayed on the display member 304, along with historical data of the concentration levels of the bioanalyte.

The present invention also provides a method for an accurate detection and quantitative measurement of creatinine bioanalyte in a bio-sample. The desired biological samples such as blood or urine are collected in very small volumes i.e., in the range of micro litres (µL), from human subjects, with a minimally invasive means, by following standard protocols. The biological samples are collected by using the device of the present invention. In the method of present invention, the preferred volume of the biological sample that can be used for the measurement of bioanalyte is preferably in the range of 1-300 micro litres (µL). The required volume of the biological sample is subject to the size of the surface area of the receptor of the device. The reduced collection of sample substantially reduces trauma in the subjects, since it is obtained through a minimally invasive sample extraction technique. The reduced volume of biological samples avoids the need for a user to resort to phlebotomy collection products.

In the method of the present invention, the determination and accurate measurement of a bioanalyte, is performed by implementing the principle of electrochemistry. Accordingly, the bioanalyte that is advantageously selected for its measurement is creatinine through a measurement of redox current flowing through the electrochemically active and creatinine-binding devices, on the application of an electric potential. The method of the present invention also measures albumin, by using the device of the present invention along with the measurement of creatinine to determine ACR.

The method of measurement of albumin bioanalyte is described in the Applicant's co-pending PCT Application No. PCT/IB2015/056619 and the contents of which are incorporated herein by reference.

In the present invention the receptor substance for creatinine is selected from creatinine-binding and electrochemically active receptor, which is advantageously a creatinine-binding and electrochemically active metal, preferably iron ($Fe^{+2}$ and $Fe^{+3}$), palladium ($Pd^{+2}$), platinum ($Pt^{+2}$) and metal halide ions thereof. The preferable halide ions are chloride and sulphate ions. In another aspect, the creatinine-binding and electrochemically active receptor is a combination of methylene blue (MB) and creatinine-binding and electrochemically active metal, preferably iron ($Fe^{+2}$ and $Fe^{+3}$), palladium ($Pd^{+2}$), platinum ($Pt^{+2}$) and the metal halide ions such as chloride or sulphate ions.

In another aspect of present invention, the receptor substance for binding urine albumin is selected from at least an organic, inorganic or a metal porphyrin substance, preferably, hemin, hematin, alkaline hematin, copper chloride ($CuCl_2$) and a salt of copper (Cu(II)). In yet another aspect, the urine albumin-binding receptor is a combination of methylene blue (MB) and one of hemin, hematin, alkaline hemin, alkaline hematin, copper chloride ($CuCl_2$) or a salt of copper (Cu(II)).

In the method of present invention, the receptor substance for binding urine creatinine is prepared, advantageously as a solution of preferred chemical substances as hereinafter described. For instance, incase $FeCl_3$ is selected as a preferred receptor, $FeCl_3$ is dissolved preferably in an aqueous solution or any other solvents, which can dissolve these substances.

In the event, methylene blue (MB) is used as a receptor, the chemical substance is preferably dissolved in distilled water or any other solvents, which can dissolve this chemical substance.

The receptor solution thus prepared is applied to the electrode members or on the membranes of the device, prior to the application of desired biological samples, containing albumin/creatinine bioanalytes.

Alternately, the receptor solution can also be premixed with the desired biological samples and the mixed solution is applied to the electrode members or on membranes of the device.

Figure 8:
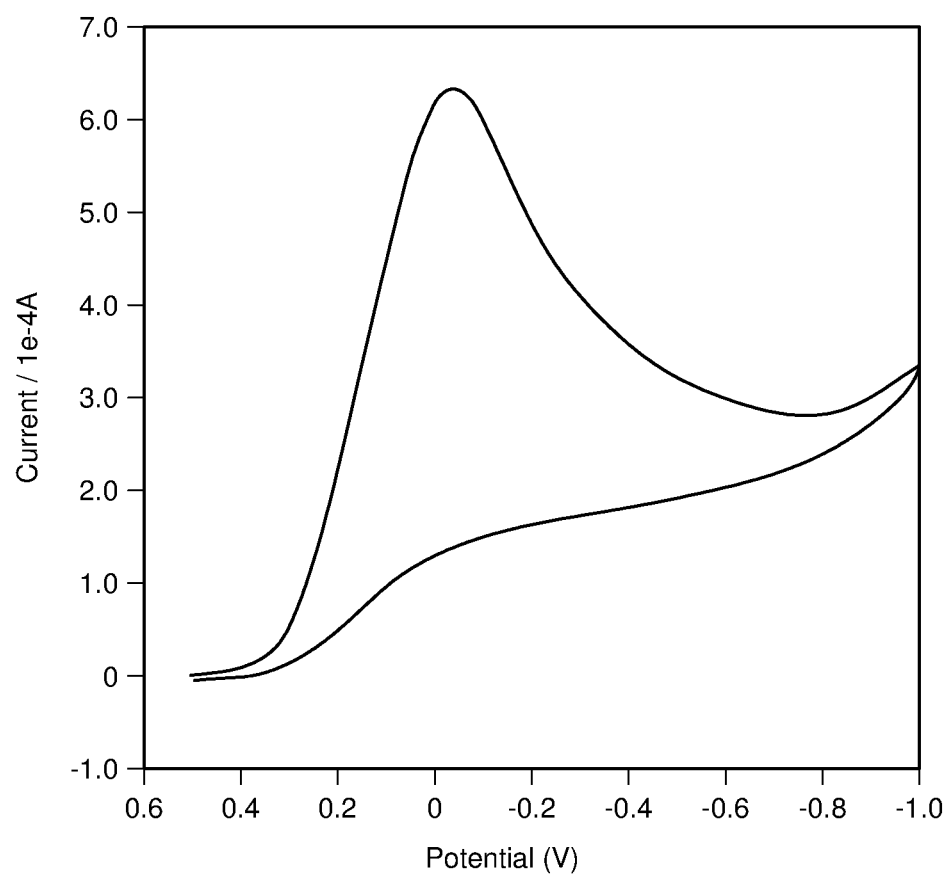
FIG. 8 is an exemplary cyclic voltammogram of $FeCl_3$ of the receptor of the device of the present invention exhibiting a reduction peak due to binding of creatinine to Fe(III).

In an exemplary aspect, the process steps for detection and measurement of urine creatinine are now described. In order to detect and measure creatinine in a urine sample, the reduced volume of the biological sample (urine) is brought in chemical contact with the receptor of the device of the present invention. The receptor is a Fe(III) substance, which is $FeCl_3$. Creatinine binds substances such as iron ($Fe^{+2}$ and $Fe^{+3}$), palladium ($Pd^{+2}$), platinum ($Pt^{+2}$). $FeCl_3$ contains iron in ferric form (Fe(III)) and this gets reduces to ferrous (Fe(II)) form, under cyclic voltammetry, as shown in the equation $Fe(III)+e^- \rightarrow Fe(II)$. The corresponding reduction peak thus obtained is shown in FIG. 8. In view of binding of creatinine to Fe(III) and Fe(III)) exhibiting a reduction current peak, $FeCl_3$ is selected as a ligand receptor, to detect creatinine concentration in the biological sample. The peak reduction current of free Fe(III) as shown in FIG. 8, is used to compare the variance in the corresponding peak reduction current, when Fe(III) binds creatinine in the urine samples.

Prior to the measurement of creatinine concentration in desired biological sample, data pertaining to standard creatinine concentrations (mg/dL) in various urine samples are collected and stored in a database member. Thus the database member is populated with the values of standard urine creatinine concentrations (mg/dL) along with the corresponding redox current values ($\mu A$) of Fe(III). The preferred redox current values for the designated concentrations are obtained in an iterative manner, where repeated tests, produce identical redox current values, for the selected creatinine concentration.

Figure 9A:
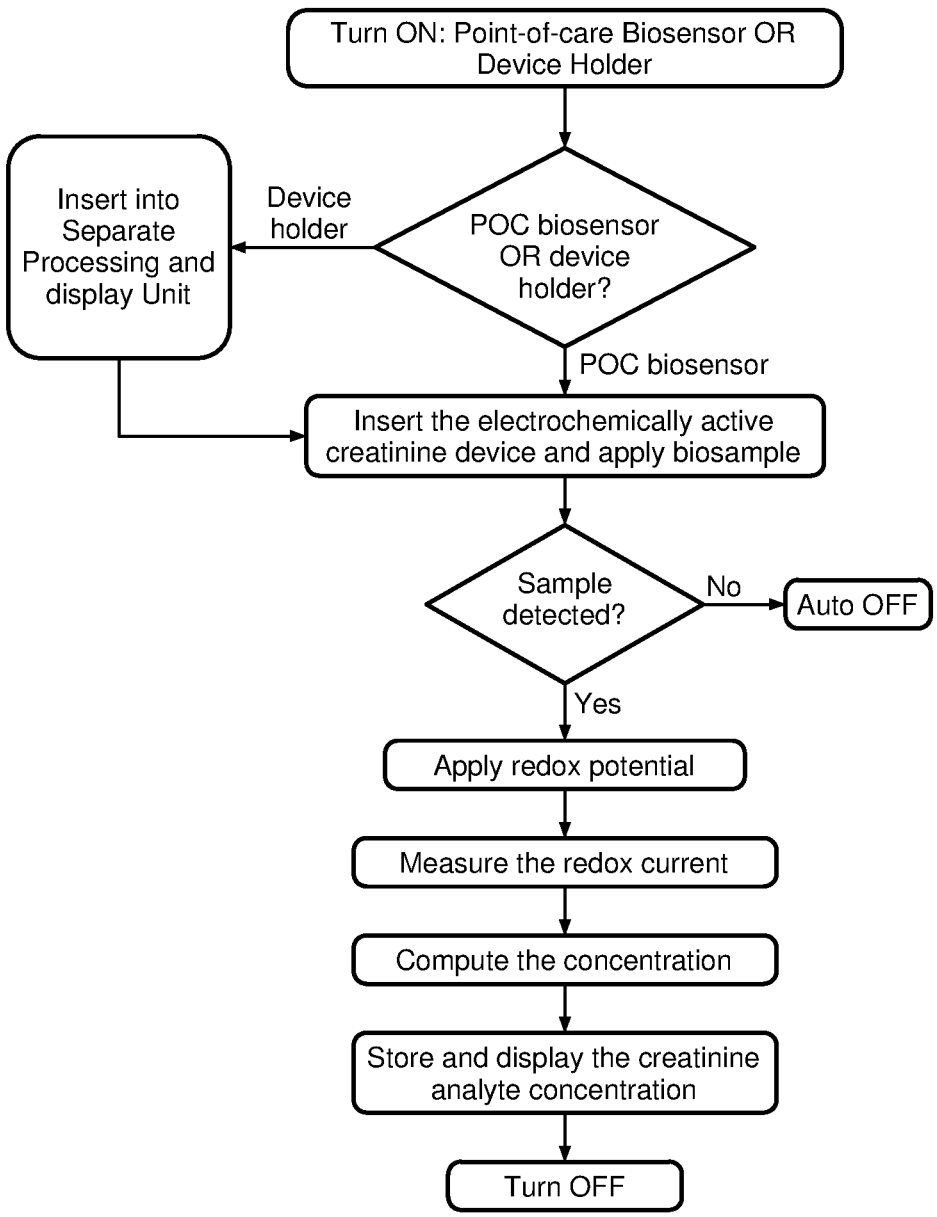
FIG. 9(a) is an exemplary high-level flow chart depicting process steps to measure quantitatively the concentration of the bioanalytes by using the device and point-of-care biosensor of the present invention.
Figure 9B:
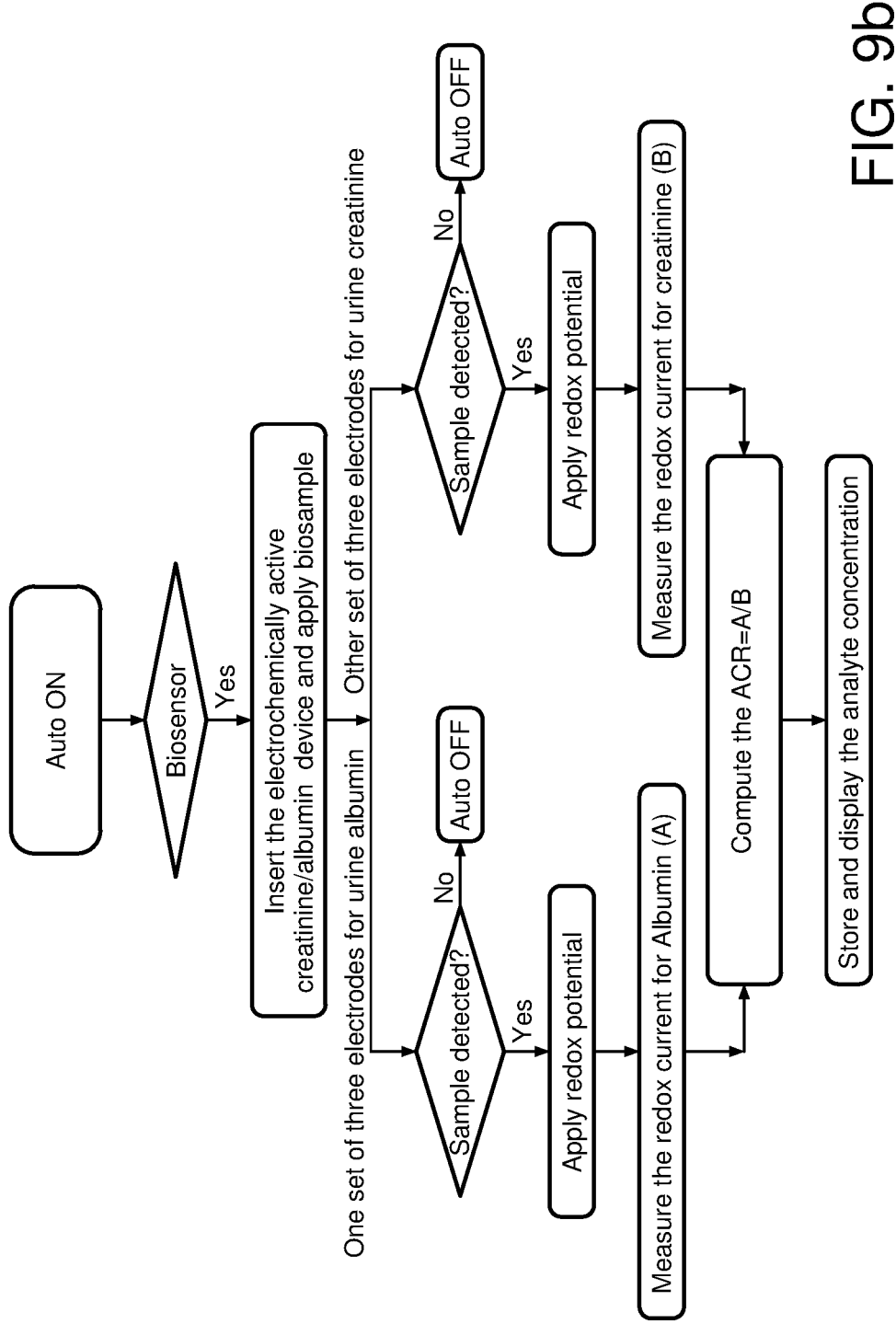
FIG. 9(b) is an illustrative high-level flow chart depicting process steps to measure quantitatively the ratio of the bioanalytes by using the device and point-of-care biosensor of the present invention.

Now, process steps to measure creatinine and albumin bioanalytes and ACR are described by particularly referring FIG. 9(*a*) and FIG. 9(*b*). Initially, the biosensor of the present invention is selected and powered on. The device is then loaded into the biosensor. The biosensor is adapted to detect the designated device. Once the device is detected by the biosensor, the device is then loaded with the desired biological sample and a desired redox potential is applied by digital-to-analog converter (DAC) to the working electrode of the device, with respect to the reference electrode. Reduction potential is a measure of the tendency of a chemical substance to acquire electrons and thereby be reduced. It is understood here that each chemical substance has its own intrinsic redox potential. The more positive the potential, the greater is the substance affinity for electrons and the tendency to be reduced. Accordingly, the redox potential of iron in NaCl buffer solution can be around −0.12 V. The redox current that is passing through the counter and working electrodes is measured by using current-to-voltage (I to V) converter.

The measured redox current is then matched with the stored redox current values and the matching urine creatinine concentration is secured and displayed by the biosensor. Alternately, the linear-fit equation can also be used to compute the concentration of bioanalyte by using the redox current value. The biosensor after having extracted the value of concentration of creatinine in the urine sample displays the value.

In order to measure the ACR, initially the biosensor is turned on and then an electrochemically active creatinine and albumin binding device is inserted into the biosensor and the biosensor circuitry applies the appropriate redox potential to the device. The biosensor reads the redox current values for both albumin and creatinine in parallel and calculates the concentrations of urine albumin and urine creatinine by the linear fit equation in the storage component. Then CPU of the biosensor calculates the ratio of urine albumin and creatinine and display the ACR value.

Figure 10:
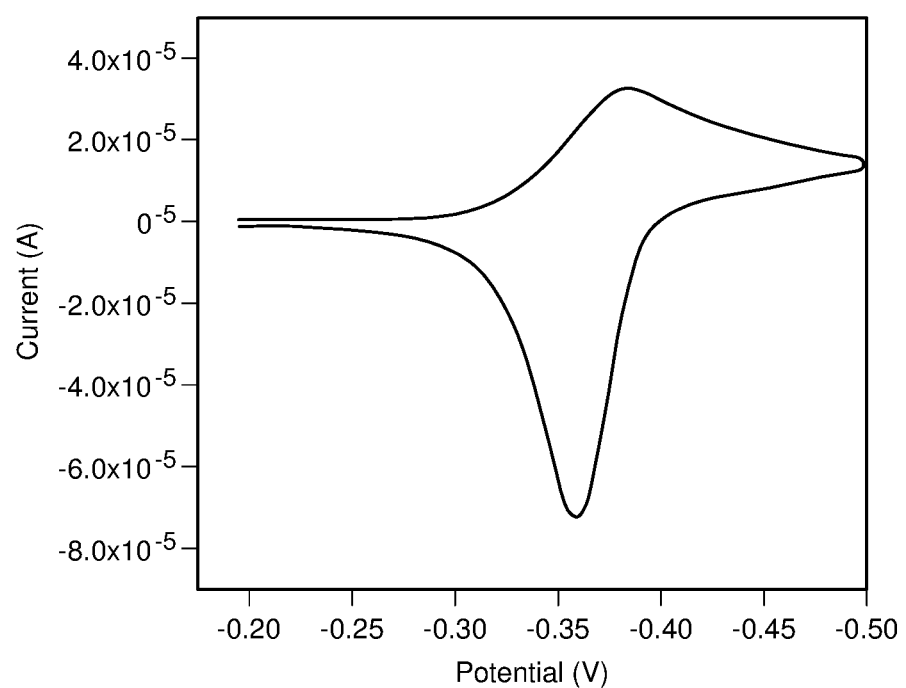
FIG. 10 is an exemplary cyclic voltammogram of methylene blue (MB) exhibiting reversible redox peaks

Methylene blue (MB) is a well-known electrochemical redox-dye. MB demonstrates a reversible redox peaks in cyclic voltammogram as shown in FIG. 10. MB is commonly used in biology for DNA staining and as an antidote for methaemoglobinaemia disorder. In methaemoglobinaemia treatment, MB reduces (by gaining electrons) into leucomethylene blue (LMB), in the presence of nicotinamide adenine dinucleotide phosphate (NADPH) enzyme.

Thereafter, LMB donates its electron to the ferric form ($Fe^{+3}$) of iron in methemoglobin molecule and converts it back into ferrous form ($Fe^{+2}$) in hemoglobin molecule. In the present invention, MB is reduced into LMB by electrochemical route using cyclic voltammetry technique. If any $Fe^{+3}$ containing element or an elemental ferric iron is added in the reduced form of the MB (LMB), then MB donates its electron to ferric form ($Fe^{+3}$) and reduces it into ferrous form of iron ($Fe^{+2}$). In this reaction, LMB is further oxidized into MB form while Iron in $Fe^{+3}$ form reduced into Iron $Fe^{+2}$ form, as shown in the following reaction:

$$MB+2e^-+H^+ \rightarrow LMB$$

$$LMB+2Fe^{+++} \rightarrow MB+2Fe^{++}$$

Figure 11:
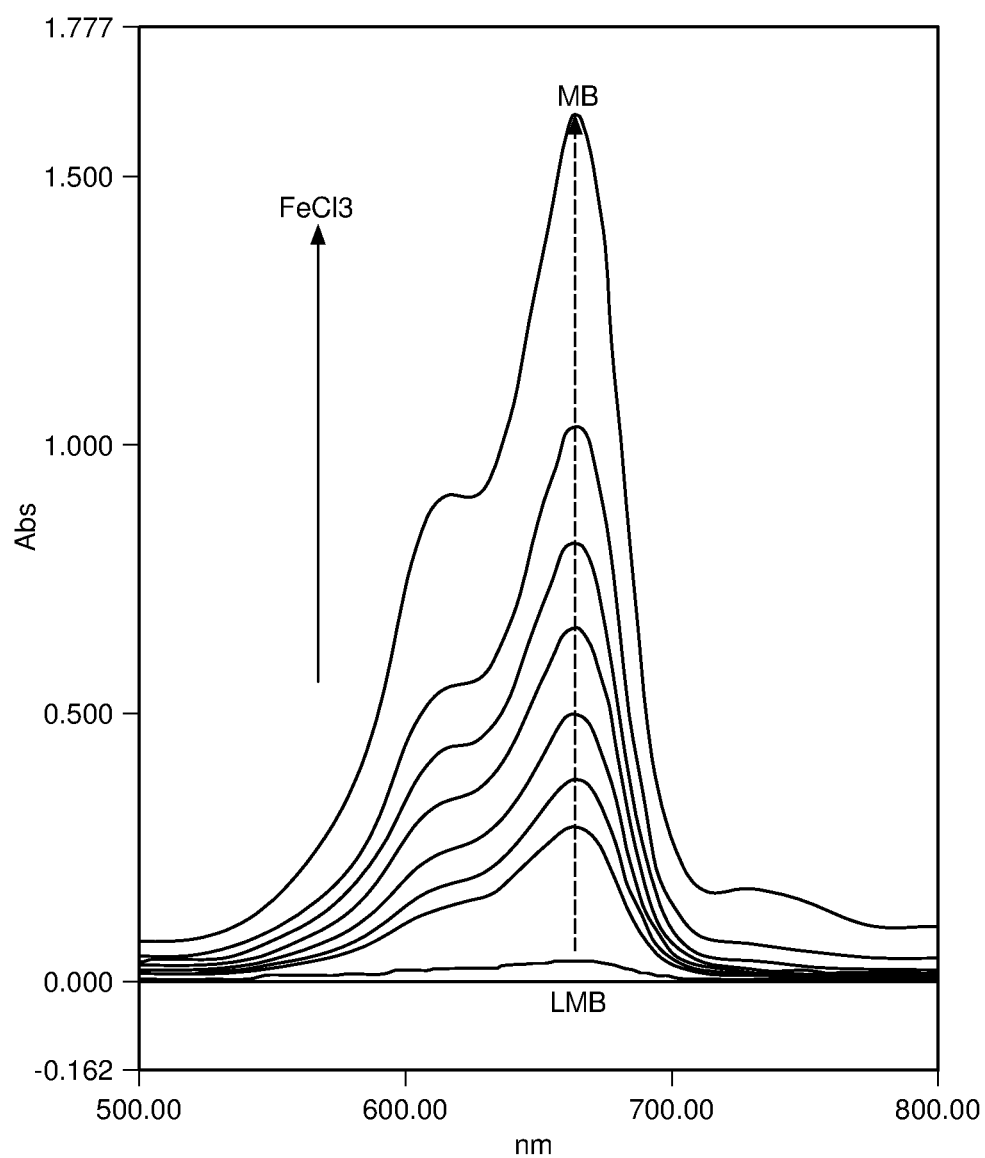
FIG. 11 depicts an exemplary UV-VIS spectra of leucomethylene blue with different concentrations of $FeCl_3$.

The reduction current peak of MB increases after adding the $FeCl_3$ because of catalytic current flow due to the donation of electrons from LMB to $Fe^{+3}$, as shown in FIG. 12. This reaction is analyzed using ultraviolet visible (UV-VIS) spectroscopy. MB demonstrates an absorption peak at about 660 nm, while LMB is a colorless liquid and it does not show any absorption peak in UV-VIS spectrum. Here, LMB solution is prepared by chemical reduction of MB using ascorbic acid. After adding the $FeCl_3$ in LMB solution, LMB oxidizes into MB by donating its electrons to Fe(III) and MB peaks appears as shown in FIG. 11.

Based on aforementioned principle of activity of $FeCl_3$ with MB, in the method of present invention a combination of $FeCl_3$-MB based receptor is adopted for creatinine detection.

In $FeCl_3$-MB based creatinine detection, the higher peak reduction current thus measured even at lower $FeCl_3$ concentration is attributed to reduction of $FeCl_3$ by LMB by donating electrons and some $FeCl_3$ molecules directly reduce at the electrode surface, similar to the case of direct detection. A small amount of MB acts as a current amplifier.

In $FeCl_3$ based direct detection of urine creatinine, the Fe(III) is reduced on the electrode surface and a corresponding reduction current is obtained. Whereas, in the case of MB-$FeCl_3$ based detection, Fe(III) is also reduced by the donation of electrons from LMB molecule to the Fe(III) molecule and hence similar peak current in MB-$FeCl_3$ based detection is obtained, even at lower $FeCl_3$ concentration.

The measured redox current is matched with the stored redox current values and the matching urine creatinine concentration is secured and displayed by the biosensor. Alternately, the linear-fit equation can also be used to compute the concentration of bioanalyte by using the redox current value. The biosensor after having extracted the value of concentration of creatinine in the urine sample displays the value.

In another aspect of the present invention urine is used as a biological sample to determine albumin to measure albumin to creatinine ratio (ACR). The aforementioned receptors, which are electrochemically active and albumin-binding are used with this biological sample along with the steps as described above, to determine the ACR.

The subject matter of the invention is now illustrated in the form of the following examples. These examples are provided for purpose of illustration and shall not be construed as limiting the scope of the invention.

Example 1: Determination of Creatinine Concentration and Corresponding Reduction Current Using $FeCl_3$ as a Receptor in Biological Urine Sample NaCl buffer with pH 6.6 solution is prepared by dissolving 500 mg of NaCl, in 100 ml of distilled water. 40 mg of human creatinine (Sigma-Aldrich) is dissolved in 10 ml of NaCl buffer to prepare the creatinine master solution and 300 mg. $FeCl_3$ is dissolved into 10 ml NaCl buffer. The 20 uL volume of $FeCl_3$ solution is used as a receptor for creatinine detection. From the master solution, different concentrations of creatinine are prepared by appropriate dilution. A constant volume of receptor (such as 20 μL) is premixed with varying concentrations of creatinine solution, to obtain a final volume 300 μL, which is used for testing.

Figure 12A:
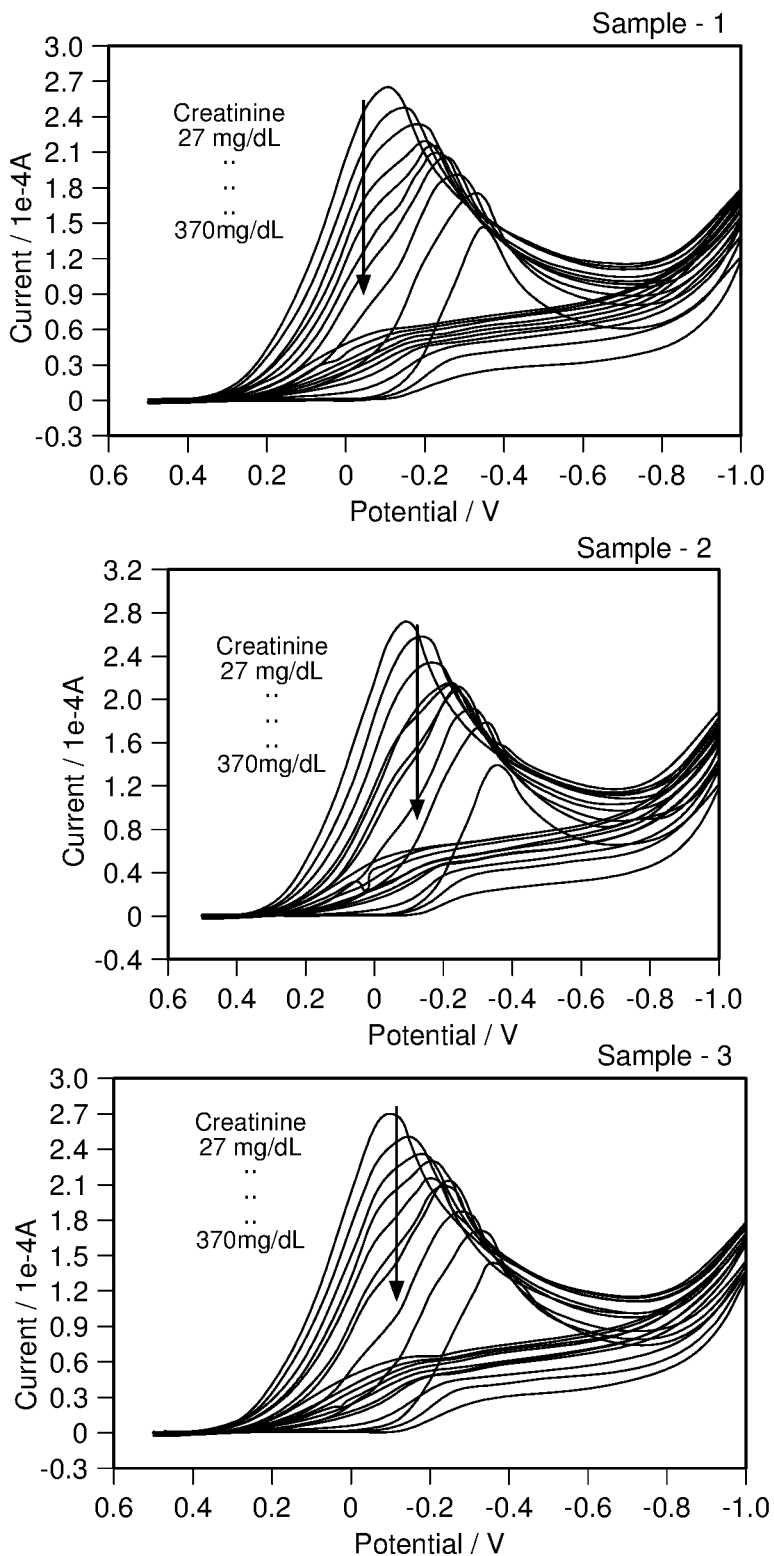
FIG. 12(a) depicts an exemplary cyclic voltammogram of free $FeCl_3$ with different urine creatinine concentrations.

A desired volume of the biological sample is taken and dispensed on the electrode of the biosensor device and the corresponding cyclic voltammogram is obtained by the CHI-Electrochemical workstation using the potential window varying from 0.6 V to −1.0 V with scan rate of 0.1 V/sec., as shown in FIG. 12(a).

Figure 12B:
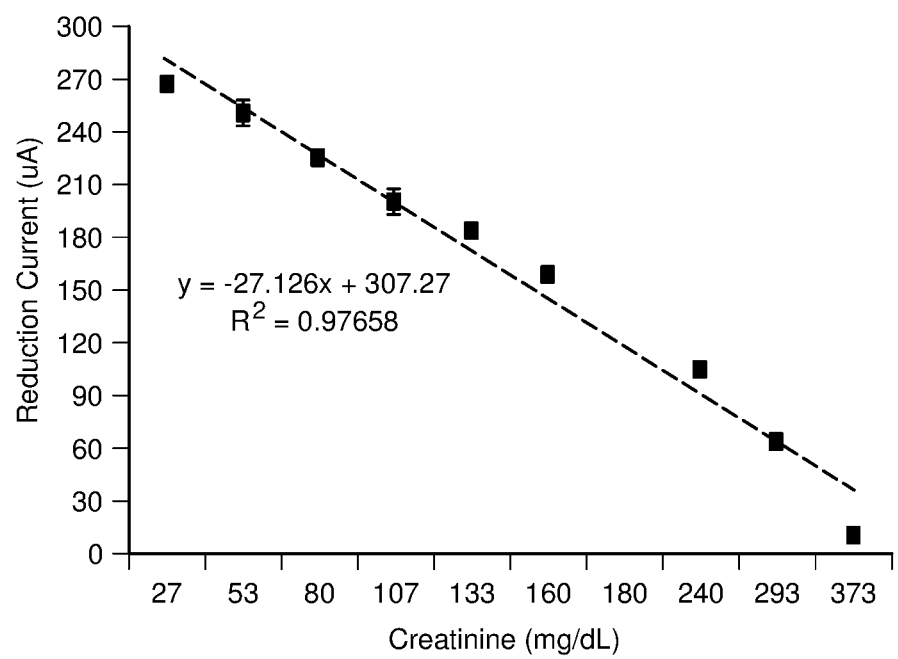
FIG. 12(b) depicts an exemplary reduction current plot versus urine creatinine concentration.

The creatinine content in the biological sample binds $FeCl_3$, thereby demonstrating a linear decrease in peak reduction current with urine creatinine concentration as shown in FIG. 12(a) and FIG. 12(b). If the concentration of creatinine in urine sample is increased, then the creatinine increasingly binds with iron thereby reducing the free iron, Fe(III) concentration on the electrode resulting in the decrease in peak reduction current of free iron.

The values of concentrations of the urine creatinine (mg/dL) along with corresponding reduction current values (μA) are recorded and tabulated as shown in Table 1. Table 1 can be prepared from linear fit equation as given below:

$$y = -27.126x + 307.27$$

Where:
y=redox current value
y=the concentration of urine creatinine

TABLE 1

| Urine Creatinine Concentration (mg/dL) | Reduction current (μA) |
|---|---|
| 27 | 267 |
| 53 | 250 |
| 80 | 225 |
| 107 | 192 |
| 133 | 183 |
| 160 | 159 |
| 240 | 105 |
| 373 | 10 |

Example 2: Measurement of Urine Creatinine with $FeCl_3$ Receptor

A sample volume of creatinine sample of 300 uL is placed on the electrode having the $FeCl_3$ receptor of 0.6 mg then the peak reduction current value is noted from cyclic voltammogram specifying a potential window from 0.6 V to −1.0 V with scan rate of 0.1 V/sec in CHI Electrochemical workstation. The value of peak reduction current is measured as 105 μA. The presence of this current value is searched in the values as provided in Table 1 and the corresponding concentration of urine creatinine is retrieved, which is 240 mg/dL.

Example 3: Determination of Creatinine Concentration and Corresponding Reduction Current Using $FeCl_3$-MB as a Receptor in Urine Physiological Range NaCl buffer with pH 6.6 solution is prepared by dissolving 500 mg of NaCl, in 100 ml of DI water. 40 mg of Human creatinine (Sigma-Aldrich) is dissolved into 10 ml of NaCl buffer to prepare the creatinine master solution and 300 mg $FeCl_3$ is dissolved into 10 ml NaCl buffer. 33.3 mg MB is dissolved into 10 ml NaCl buffer. The 20 uL volume of $FeCl_3$ plus 304 volume of MB solution is used as a receptor for creatinine detection. From the master solution, different concentrations of creatinine are prepared by appropriate dilution. A constant volume of receptor (such as 50 µL) is premixed with varying concentration of creatinine solution to get a final volume 300 µL for testing.

Figure 13A:
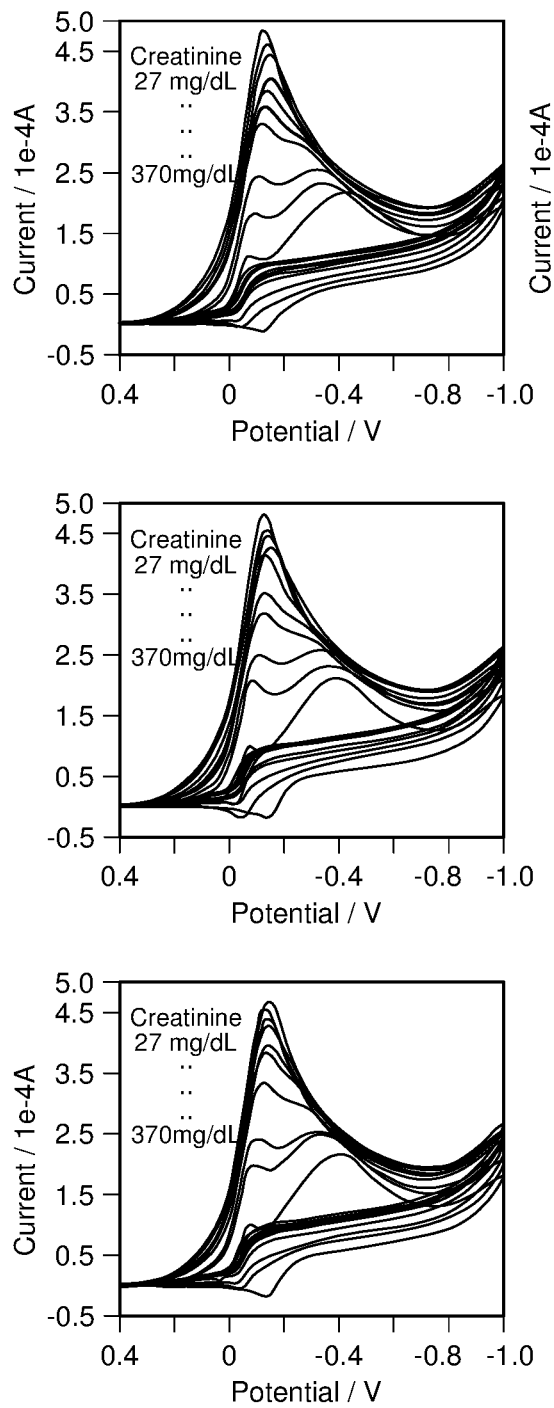
FIG. 13(a) is an exemplary cyclic voltammogram of free $FeCl_3$ and MB with different urine creatinine concentrations.

A desired volume of the biological sample is taken and dispensed on the electrode of the biosensor device and the corresponding cyclic voltammogram is obtained by the CHI-Electrochemical workstation using the potential window varying from 0.6 V to −1.0 V with scan rate of 0.1 V/sec., as shown in FIG. 13(a).

Figure 13B:
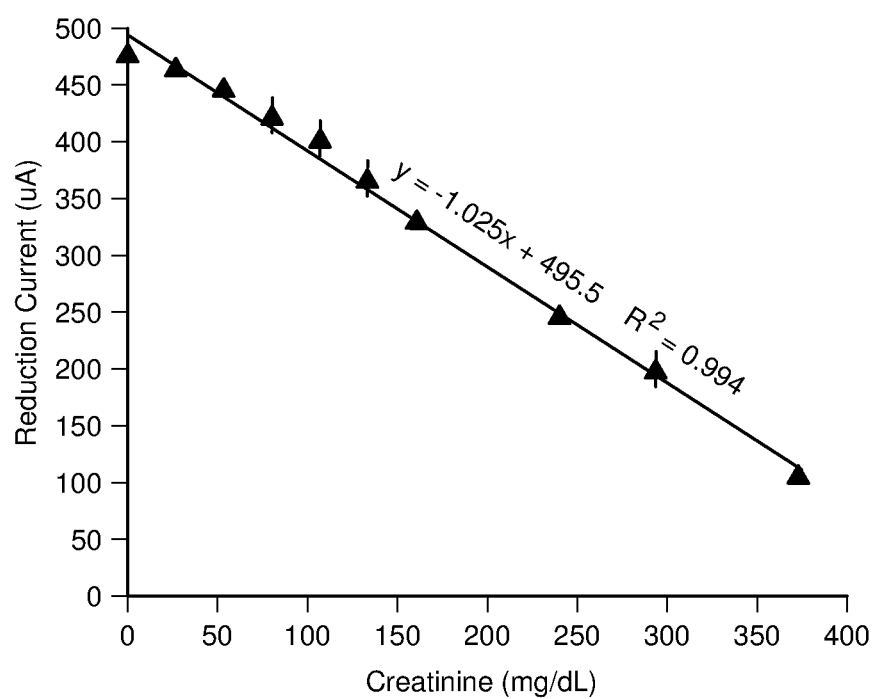
FIG. 13(b) depicts an exemplary reduction current plot versus urine creatinine concentration.

The creatinine content in the sample binds $FeCl_3$, thereby demonstrating a linear decrease in peak reduction current with urine creatinine concentration as shown in FIG. 13(a) and FIG. 13(b). If the concentration of creatinine in urine sample is increased, then the creatinine increasingly binds with iron thereby reducing the free iron, Fe(III) concentration on the electrode resulting in the decrease in peak reduction current of free iron.

The values of concentrations of the urine creatinine (mg/dL) along with corresponding reduction current values (µA) are recorded and tabulated as shown in Table 2. Table 2 can be prepared from linear fit equation as given below:

$$y=-1.6x+495.5$$

Where:
y=redox current value
x=the concentration of urine creatinine

TABLE 2

| Urine Creatinine Concentration (mg/dL) | Reduction current (µA) |
| --- | --- |
| 27 | 470 |
| 53 | 448 |
| 80 | 425 |
| 107 | 400 |
| 133 | 375 |
| 160 | 350 |
| 240 | 324 |
| 373 | 110 |

Example 4: Measurement of Urine Creatinine with $FeCl_3$-MB Receptor

A sample volume of creatinine sample of 300 uL is placed on the electrode having the MB-$FeCl_3$ receptor of 0.6 mg and then the peak reduction current value is observed from cyclic voltammogram by varying a potential window from 0.6 V to −1.0 V, with scan rate of 0.1 V/sec in CHI-Electrochemical workstation. The value of peak reduction current is noted 110 µA. The presence of this current value is searched in the Table 2 and the corresponding concentration of urine creatinine is obtained is 373 mg/dL.

Example 5: Determination of Values of Urine Albumin Concentration and Corresponding Reduction Current Using MB-Hemin as a Receptor Synthetic urine is prepared by dissolving 14.1 g of NaCl, 2.8 g KCl, 17.3 g of urea, 19 ml ammonia water (25%), 0.60 g $CaCl_2$ and 0.43 g $MgSO_4$ in 0.02 mole/L of HCl. The final pH of synthetic urine is adjusted to 6.04 with using HCl and ammonia water. MB is dissolved in DI water and hemin is dissolved in an alkaline solution. A combination of MB and Hemin solution is used as a receptor (for example 5 µL hemin plus 4 µL MB solution) for urine albumin detection. 3 mg of human albumin is dissolved in 10 ml of synthetic urine solution to prepare the micro albumin solution. 9 µL of receptor is premixed with the micro albumin solution with known concentrations and make the final volume 300 µL.

Figure 14A:
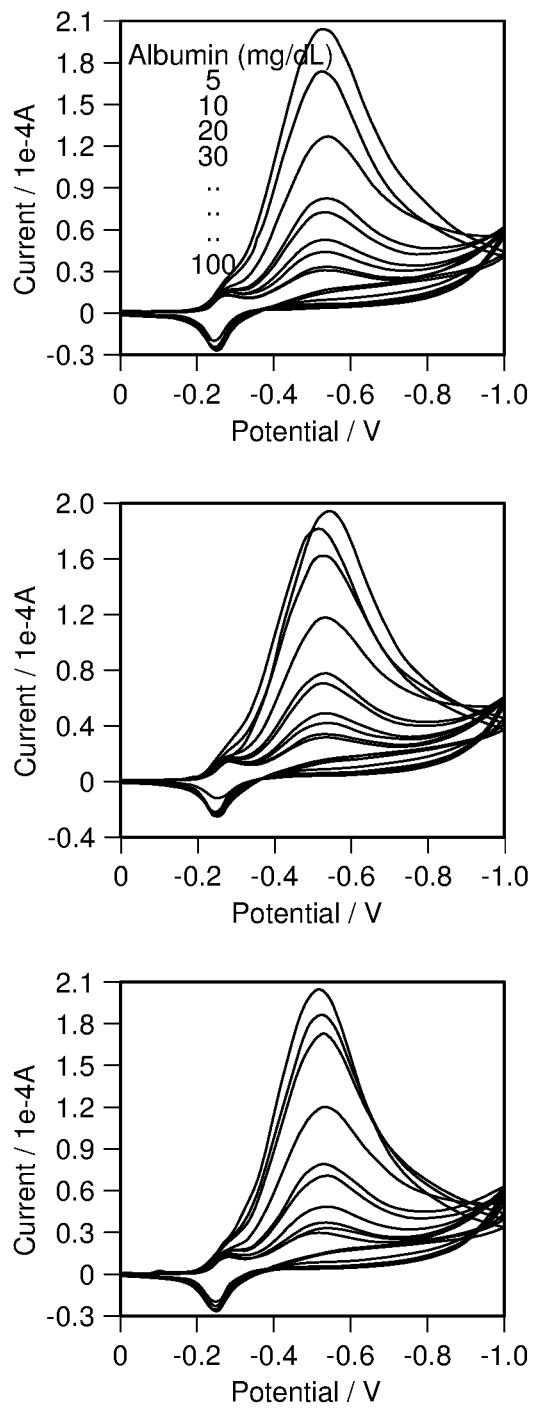
FIG. 14(a) is an exemplary cyclic voltammogram of hemin and MB with different urine albumin concentrations.

A desired volume of the biological sample (urine) is taken and dispensed on the electrode of the biosensor device and the corresponding cyclic voltammogram is obtained by the CHI-Electrochemical workstation using the potential window by varying from 0 V to −1 V with a scan rate of 0.1 V/sec, as shown in FIG. 14(a).

Figure 14B:
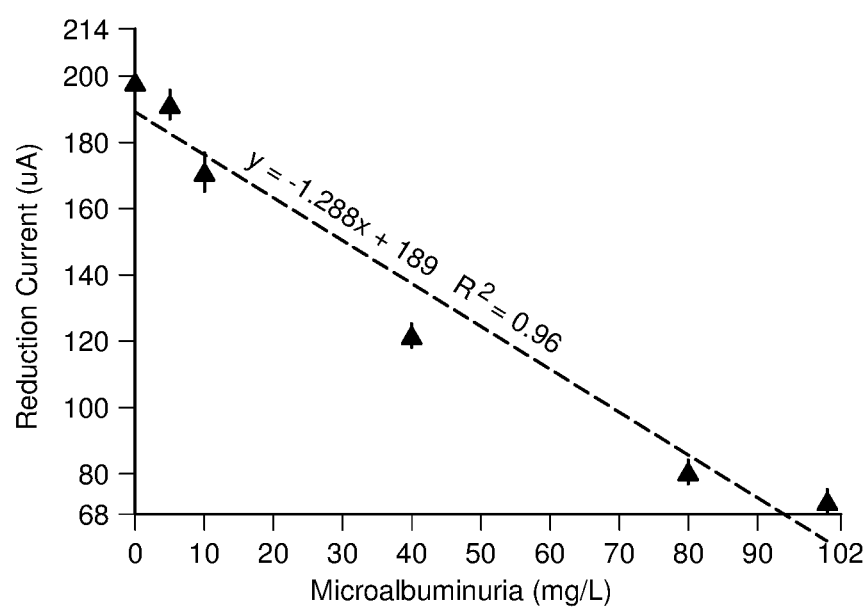
FIG. 14(b) depicts an exemplary reduction current plot versus urine albumin concentration.

Due to the catalytic current because of electron donation by LMB to hemin, we get the higher peak current even at lower concentration of hemin in comparison to the direct hemin based urine albumin detection, as described earlier. The albumin content in the urine sample binds hemin thereby demonstrating a linear decrease in peak redox current with urine albumin concentration as shown in FIG. 14(a) and FIG. 14(b). If the concentration of albumin in urine sample is increased, then the albumin increasingly binds with hemin thereby reducing the free hemin concentration on the electrode resulting in the decrease in peak redox current of free hemin.

The values of concentrations of the urine albumin (mg/L) along with corresponding reduction current values (µA) are recorded and tabulated as shown in Table 3. Table 3 can be prepared from linear fit equation as given below:

$$y=-1.288x+189$$

Where:
Y=redox current value
X=the concentration of urine albumin

TABLE 3

| Urine Albumin Concentration (mg/L) | Reduction current (µA) |
| --- | --- |
| 0 | 203.8 |
| 5 | 188.2 |
| 10 | 173.2 |
| 40 | 118 |
| 80 | 80.1 |
| 100 | 71.8 |
| 150 | 49.5 |

Example 6: MB-Hemin Based Direct Detection of Urine Albumin in Synthetic Urine A sample volume of synthetic urine of 300 µL is placed on the electrode having the MB-hemin receptor of 13.3 µg MB plus 0.5 µg hemin then the peak redox current value is noted from cyclic voltammogram specifying a potential window from 0.6 V to −0.4 V in CHI Electrochemical workstation. The value of peak reduction current is 188.2 µA. This current value is searched in the Table 3 and the corresponding concentration of urine albumin is obtained is 5 mg/L.

Example 7: Determination of Values of Urine ACR Using Hemin and FeCl3 Receptors for Urine Albumin and Urine Creatinine Respectively Synthetic urine is prepared by dissolving 14.1 g of NaCl, 2.8 g KCl, 17.3 g of urea, 19 ml ammonia water (25%), 0.60 g CaCl$_2$ and 0.43 g MgSO$_4$ in 0.02 mole/L of HCl. The final pH of synthetic urine is adjusted to 6.04 by using HCl and ammonia water.

40 mg Sigma creatinine is dissolved in 10 ml of synthetic urine solution. 3 mg of human albumin is dissolved in 10 ml of synthetic urine solution to prepare the micro albumin solution.

4 mg Sigma hemin is dissolved in 20 ml of synthetic urine, 20 μL Hemin solution is used as a receptor for urine albumin detection at different creatinine concentration.

A desired volume of the biological sample (synthetic urine) is taken and dispensed on the electrode of the biosensor device and the corresponding cyclic voltammogram is obtained by the CHI-Electrochemical workstation using the potential window, that varies from 0 V to −1 V with scan rate of 0.1 V/sec.

Figure 15:
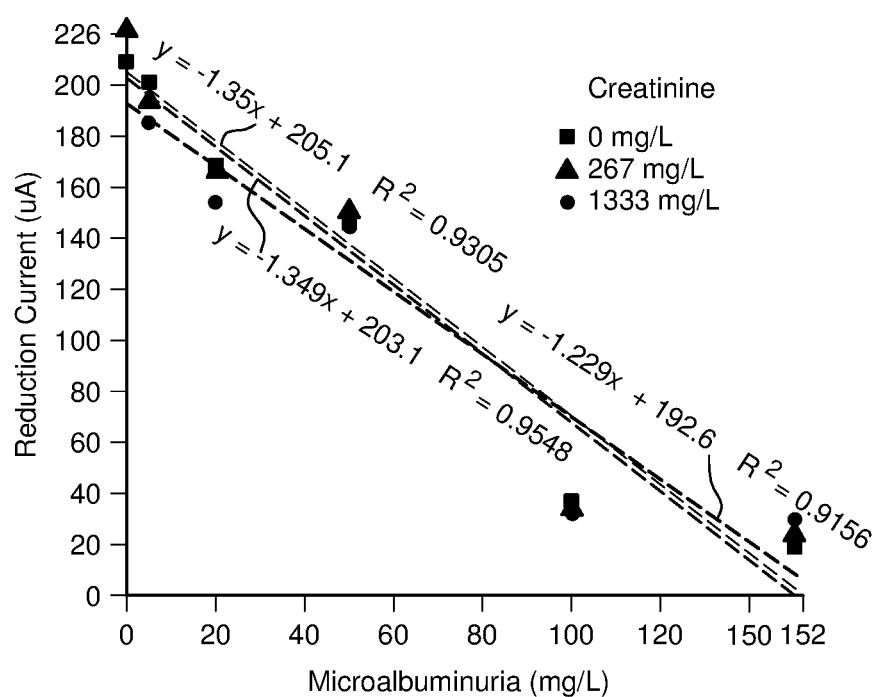
FIG. 15 illustrates a reduction current Vs. urine albumin plot with different creatinine concentrations.
Figure 16:
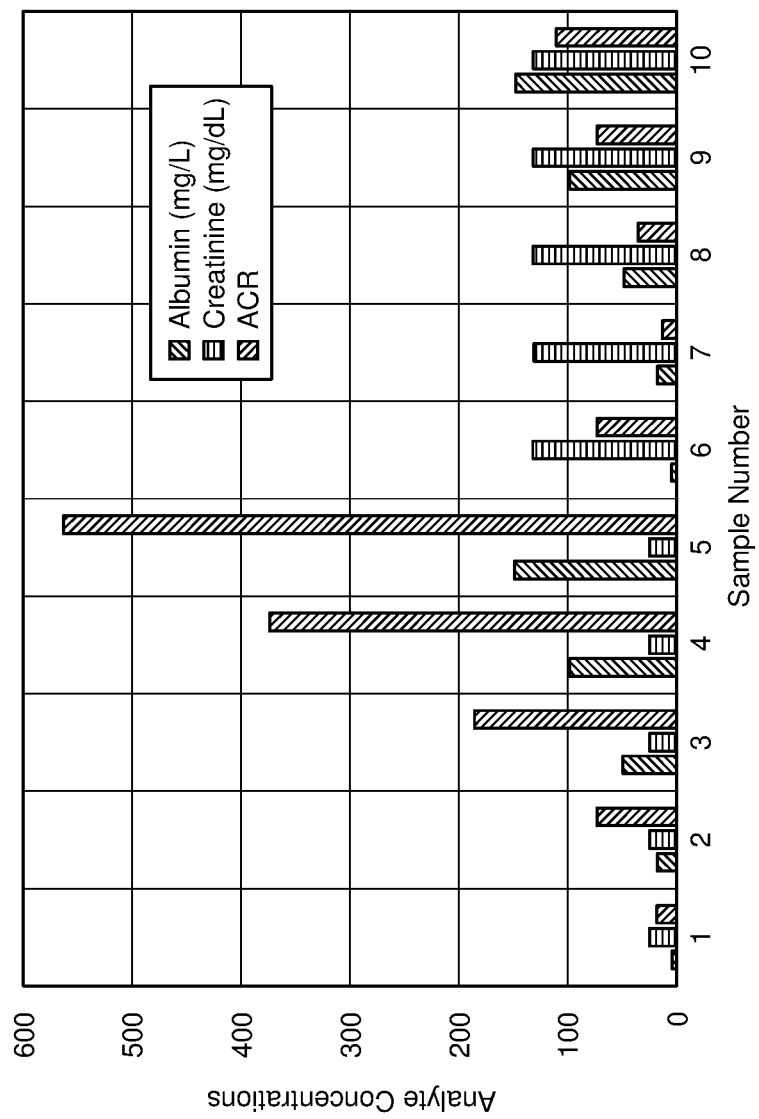
FIG. 16 illustrates concentrations of urine albumin, urine creatinine and ACR in biological samples.

The albumin content in the urine sample binds hemin thereby demonstrates a linear decrease in peak redox current with urine albumin concentration as shown in FIG. 15(a) for different creatinine concentrations. If the concentration of albumin in urine sample is increased, then the albumin increasingly binds with hemin thereby reducing the free hemin concentration on the electrode resulting in the decrease in peak redox current of free hemin. FIG. 16 shows the urine albumin concentrations, urine creatinine concentrations and calculated ACR for different samples.

The values of concentrations of the urine albumin (mg/L) and creatinine for different samples is shown in Table 4.

TABLE 4

| Sample Number | Urine albumin (mg/L) | Urine Creatinine (mg/dL) | ACR (mg/g) |
|---|---|---|---|
| 1 | 5 | 26.7 | 19 |
| 2 | 20 | 26.7 | 75 |
| 3 | 50 | 26.7 | 187 |
| 4 | 100 | 26.7 | 375 |
| 5 | 150 | 26.7 | 562 |
| 6 | 5 | 133.3 | 4 |
| 7 | 20 | 133.3 | 15 |
| 8 | 50 | 133.3 | 38 |
| 9 | 100 | 133.3 | 75 |
| 10 | 150 | 133.3 | 113 |

Example 8: Detection of Urine ACR in Synthetic Urine

The present invention uses the non-enzymatic and non-antibody based novel chemical receptors that can be adsorbed easily at the surface of printed electrodes. The albumin receptor does not interfere with Creatinine molecule and the creatinine receptor does not interfere with albumin molecule, which advantageously gives the accurate result of ACR. The calculation of Urine ACR is as given below:

ACR=Urine albumin (mg/L)/(Urine creatinine (g/L)
ACR=(20/0.267)=74.9 mg/g
For creatinine=133.3 mg/dL
ACR=(20/1.3)=15.4 mg/g Advantages of the Present Invention In the present invention non-enzymatic and non-antibody based receptors are used in conjunction with electrodes, for quantitative measurement of bioanalytes viz., Creatinine and ACR.

The present invention adopts a method of binding of human albumin and creatinine with electrochemically active receptors, which are more stable against the variations in ambient conditions, for the electrochemical detection of bioanalytes related to urine creatinine, serum creatinine and urine albumin.

The device and the biosensor of the present invention do not require special storage conditions.

In the quantitative measurement of bioanalytes of the present invention a minimal invasive technique where a reduced volume of sample volume is used.

It is also understood that the following claims are intended to cover all the generic and specific features of the invention herein described and all statements of the scope of the invention, which as a matter of language might be said to fall there between.

We claim:

1. A device, comprising:
   (i) a first electrode member, comprising either two or three electrodes, wherein said first electrode member is in chemical contact with an electrochemically active urine albumin receptor, said urine albumin receptor selected from the group consisting of hemin and hemin in combination with methylene blue:
   (ii) a second electrode member, comprising either two or three electrodes, wherein said second electrode member is in chemical contact with an electrochemically active urine creatinine receptor, said urine creatinine receptor comprising an electrochemically active metal or a combination of an electrochemically active metal and methylene blue (MB), wherein the electrochemically active metal is selected from the group consisting of:
   (a) $Fe^{+2}$ ions,
   (b) $Fe^{+3}$ ions,
   (c) $Pd^{+2}$ ions, and
   (d) $Pt^{+2}$ ions
   wherein said first and second electrode members are arranged upon a substrate.

2. The device as claimed in claim 1, wherein said urine albumin receptor is embedded in a membrane disposed on said first electrode member, and said urine creatinine receptor is embedded in a membrane disposed on said second electrode member.

3. The device as claimed in claim 1, wherein the first electrode member comprises three electrodes, and the second electrode member comprises three electrodes.

4. The device as claimed in claim 1, wherein said biological sample is urine or blood and said device is disposed in a housing and said housing is a cartridge or a cassette.

5. The device of claim 1, wherein the urine creatinine receptor is selected from the group consisting of $Fe^{+2}$ ions and $Fe^{+3}$ ions.

6. The device of claim 1, wherein the urine albumin receptor is hemin in combination with methylene blue.

7. A holder for holding a creatinine-binding and electrochemically active device, said holder comprising:
   (i) a device detection and signal conditioning means disposed in a housing;
   (ii) a USB connector disposed at one end of said housing and an electrically conductive port disposed at the other end of said housing; and
   (iii) the device as claimed in claim 1 disposed to connect to said housing through said electrically conductive port for collecting and retaining a biological sample with creatinine bioanalyte.

8. The holder as claimed in claim 7, wherein the urine creatinine receptor is selected from the group consisting of $Fe^{+2}$ ions and $Fe^{+3}$ ions.

9. A holder for holding a creatinine, urine albumin-binding and electrochemically active device, said holder comprising:
  (i) a device detection and signal conditioning means disposed in a housing;
  (ii) a USB connector disposed at one end of said housing and an electrically conductive port disposed at the other end of said housing; and
  (iii) the device as claimed in claim 1, disposed to connect to said housing through, said electrically conductive port for collecting and retaining a biological sample with creatinine and urine albumin bioanalytes.

10. The holder as claimed in claim 9, wherein the urine creatinine receptor is selected from the group consisting of $Fe^{+2}$ ions and $Fe^{+3}$ ions.

11. A point-of-care biosensor for measuring a concentration of a creatinine bioanalyte in a biological sample, said biosensor comprising:
  (i) a housing with a display member and an electrically conducting port,
  (ii) the device as claimed in claim 1, disposed to connect to said housing through said electrically conductive port for collecting and retaining a biological sample; and
  (iii) a digital controller disposed in said housing and configured to measure redox current from a redox potential applied to said device, retrieve and render creatinine bioanalyte concentration, by linearly matching the concentrations of creatinine, and optionally
  (iv) a database member with stored standard values of creatinine bioanalyte concentrations in biological samples along with reciprocal redox currents, connected to said digital controller.

12. The biosensor as claimed in claim 11, wherein the urine creatinine receptor is selected from the group consisting of $Fe^{+2}$ ions and $Fe^{+3}$ ions.

13. A point-of-care biosensor for measuring albumin to creatinine ratio (ACR) in a biological sample, said biosensor comprising:
  (i) a housing with a display member and an electrically conducting port,
  (ii) the device as claimed in claim 1, disposed to connect to said housing through said electrically conductive port for collecting and retaining a biological sample; and
  (iii) a digital controller disposed in said housing and configured to measure redox currents of urine creatinine and urine albumin from a redox potential applied to said device, to calculate albumin to creatinine ratio in said urine sample and render albumin to creatinine ratio (ACR) by linearly matching the concentrations of urine creatinine and urine albumin with corresponding redox currents;
  (iv) a database member with stored standard values of urine creatinine and urine albumin bioanalyte concentrations in urine samples along with reciprocal redox currents, connected to said digital controller.

14. The biosensor as claimed in claim 13, wherein the urine creatinine receptor is selected from the group consisting of $Fe^{+2}$ ions and $Fe^{+3}$ ions.

15. A method for measuring a concentration of creatinine bioanalyte in a biological sample, comprising the steps of:
  (i) applying a redox potential to the device of claim 1 with a reduced volume of a biological sample with a creatinine bioanalyte; and
  (ii) determining and rendering a concentration of said creatinine bioanalyte in said biological sample, by linearly matching with a corresponding redox current of the second electrode member.

16. The method as claimed in claim 15, wherein the urine creatinine receptor is selected from the group consisting of $Fe^{+2}$ ions and $Fe^{+3}$ ions.

17. The method as claimed in claim 15, wherein said biological sample is human blood or urine and in the range of 1-300 microlitres (μL).

18. A method for measuring the albumin to creatinine ratio (ACR) in a urine sample, comprising the steps of:
  (a) applying a redox potential to the first electrode member and second electrode member of the device as claimed in claim 1, where the first electrode member and second electrode member are loaded with a reduced volume of a urine sample with a creatinine bioanalyte and albumin bioanalyte;
  (b) determining the concentrations of urine albumin and urine creatinine bioanalytes in said urine sample, by linearly matching with corresponding redox currents of the first electrode member and second electrode member; and
  (c) determining and rendering albumin to creatinine ratio from said creatinine and albumin concentrations.

19. The method as claimed in claim 18, wherein said biological sample is human blood or urine and in the range of 1-300 microlitres (μL).

20. The method as claimed in claim 18, wherein the urine creatinine receptor is selected from the group consisting of $Fe^{+2}$ ions and $Fe^{+3}$ ions.

* * * * *